(12) United States Patent
Leblond et al.

(10) Patent No.: US 12,165,746 B2
(45) Date of Patent: Dec. 10, 2024

(54) METHODS AND SYSTEMS FOR ASSESSING A PHENOTYPE OF A BIOLOGICAL TISSUE OF A PATIENT USING RAMAN SPECTROSCOPY

(71) Applicants: Polyvalor, Limited Partnership, Montreal (CA); Frederic Leblond, Terrebone (CA); Emile Lemoine, Montreal (CA)

(72) Inventors: Frederic Leblond, Terrebone (CA); Emile Lemoine, Montreal (CA)

(73) Assignee: POLYVALOR, LIMITED PARTNERSHIP, Montreal (CA)

( * ) Notice: Subject to any disclaimer, the term of this patent is extended or adjusted under 35 U.S.C. 154(b) by 189 days.

(21) Appl. No.: 17/616,546

(22) PCT Filed: Jun. 3, 2020

(86) PCT No.: PCT/IB2020/055252
§ 371 (c)(1),
(2) Date: Dec. 3, 2021

(87) PCT Pub. No.: WO2020/245748
PCT Pub. Date: Dec. 10, 2020

(65) Prior Publication Data
US 2022/0238187 A1    Jul. 28, 2022

Related U.S. Application Data

(60) Provisional application No. 62/856,181, filed on Jun. 3, 2019.

(51) Int. Cl.
*G16B 40/10* (2019.01)
*A61B 5/00* (2006.01)
*G16B 40/20* (2019.01)

(52) U.S. Cl.
CPC ............ *G16B 40/10* (2019.02); *A61B 5/7264* (2013.01); *G16B 40/20* (2019.02)

(58) Field of Classification Search
CPC ........ G16B 40/20; G16B 40/30; G16B 40/10; G06N 20/00; G06N 7/01; A61B 5/7264
See application file for complete search history.

(56) References Cited

FOREIGN PATENT DOCUMENTS

WO    WO-2015154187 A1 * 10/2015 ........... A61B 5/0075

\* cited by examiner

*Primary Examiner* — An H Do
(74) *Attorney, Agent, or Firm* — Reno Lessard; Norton Rose Fulbright Canada LLP

(57) ABSTRACT

There is described a method of assessing a phenotype of a biological tissue of a patient. The method generally having receiving a Raman emission signal indicative of Raman emission of a portion of said biological tissue; using a feature generator, determining a value of a first feature based on said received Raman emission signal; using a computing device, receiving a value of a clinical parameter associated to the patient; generating a value of a second feature by interacting said value of said first feature with said value of said clinical parameter; using a trained assessment engine, assessing the phenotype of the biological tissue based on at least said value of said second feature; and outputting a signal based on said assessment.

20 Claims, 13 Drawing Sheets

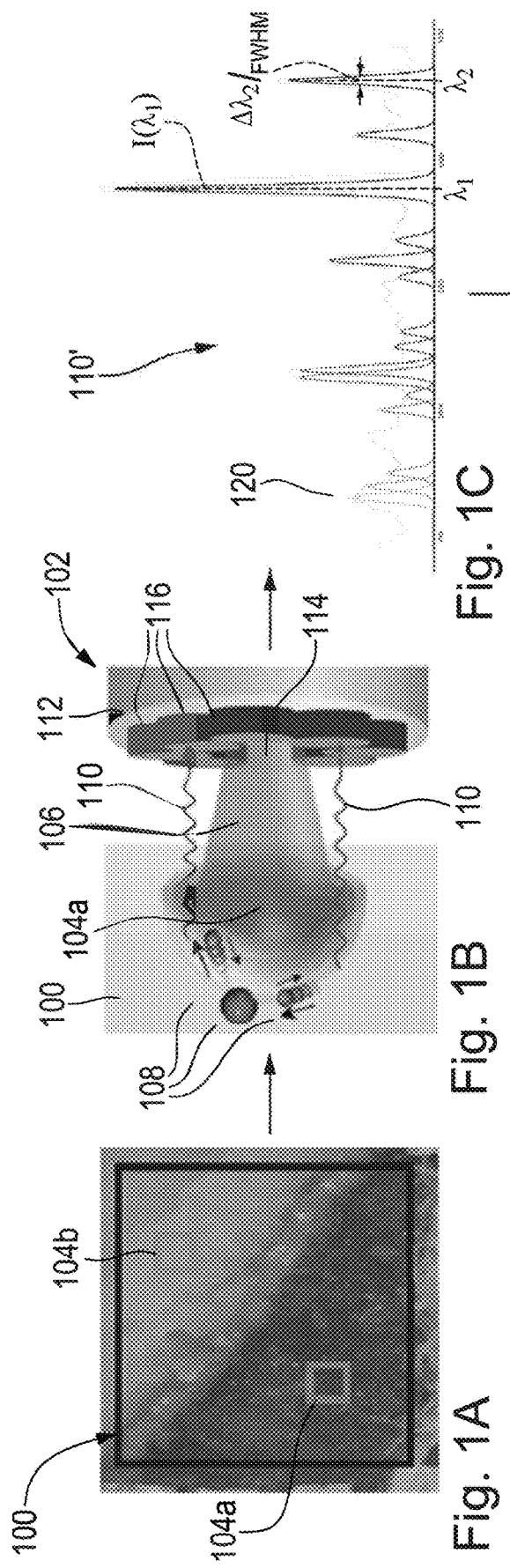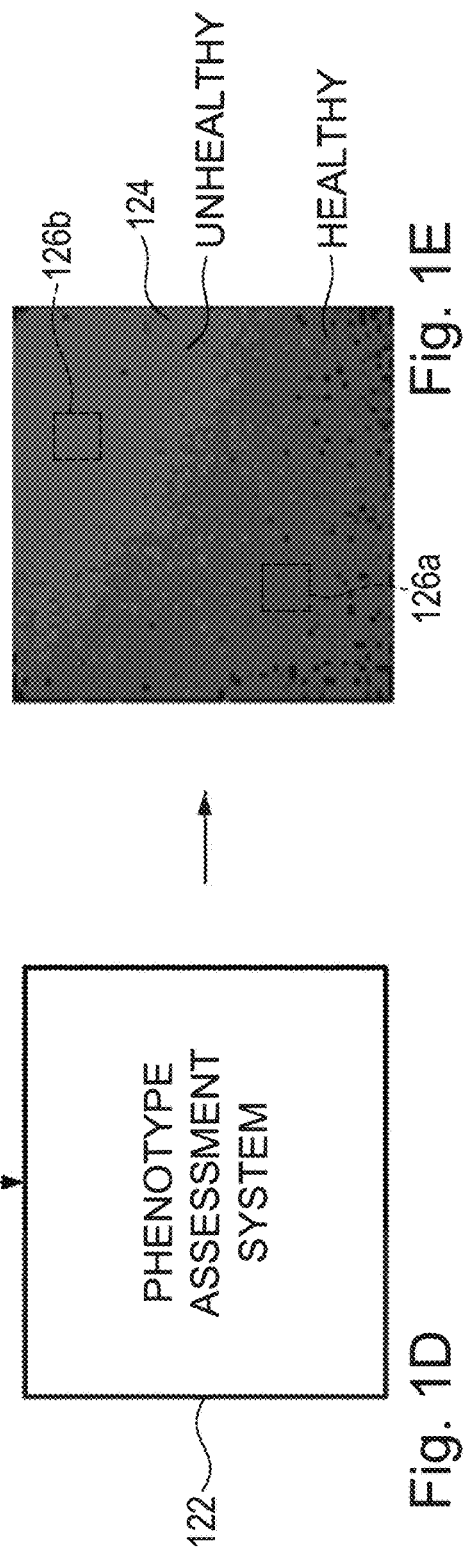

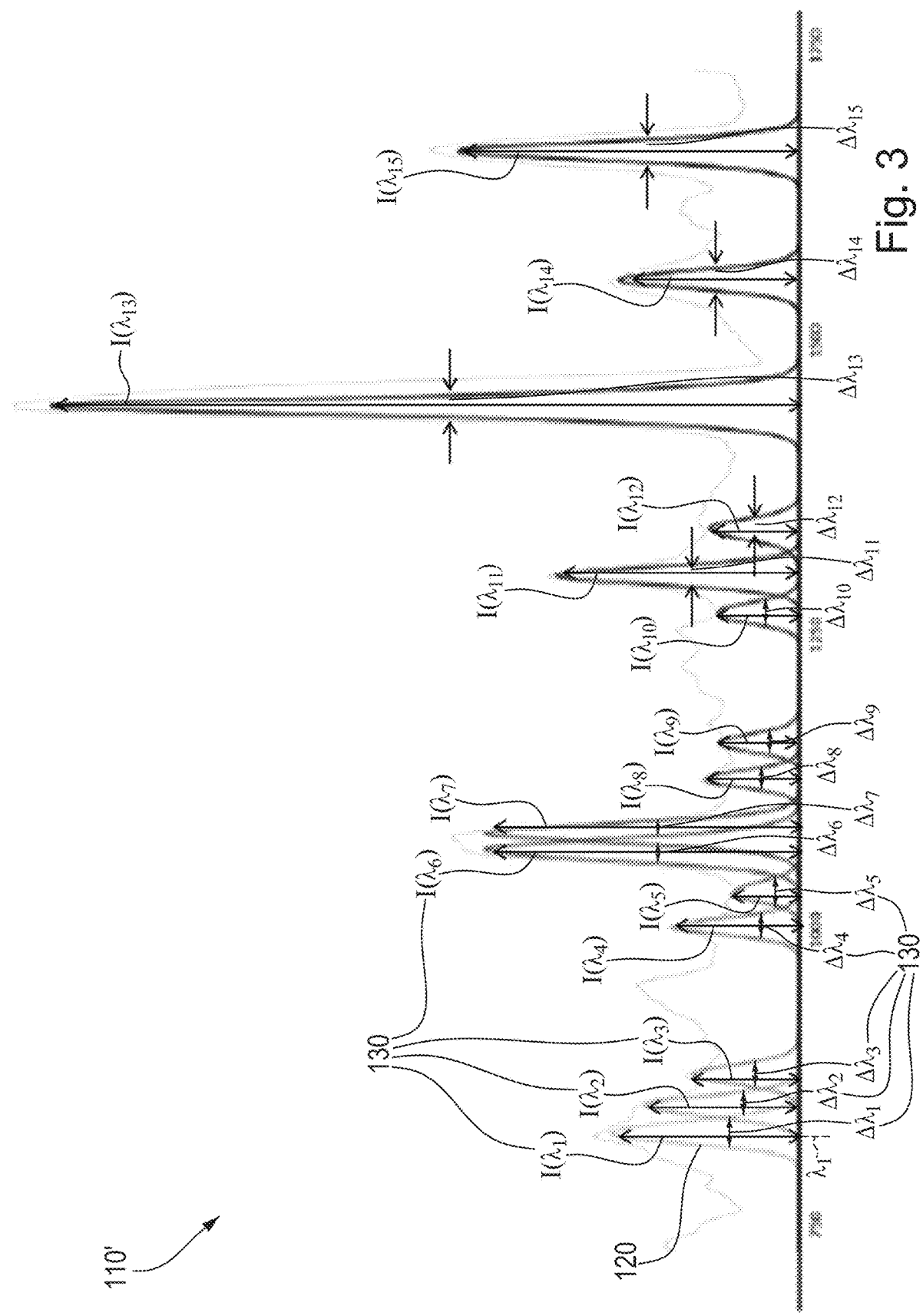

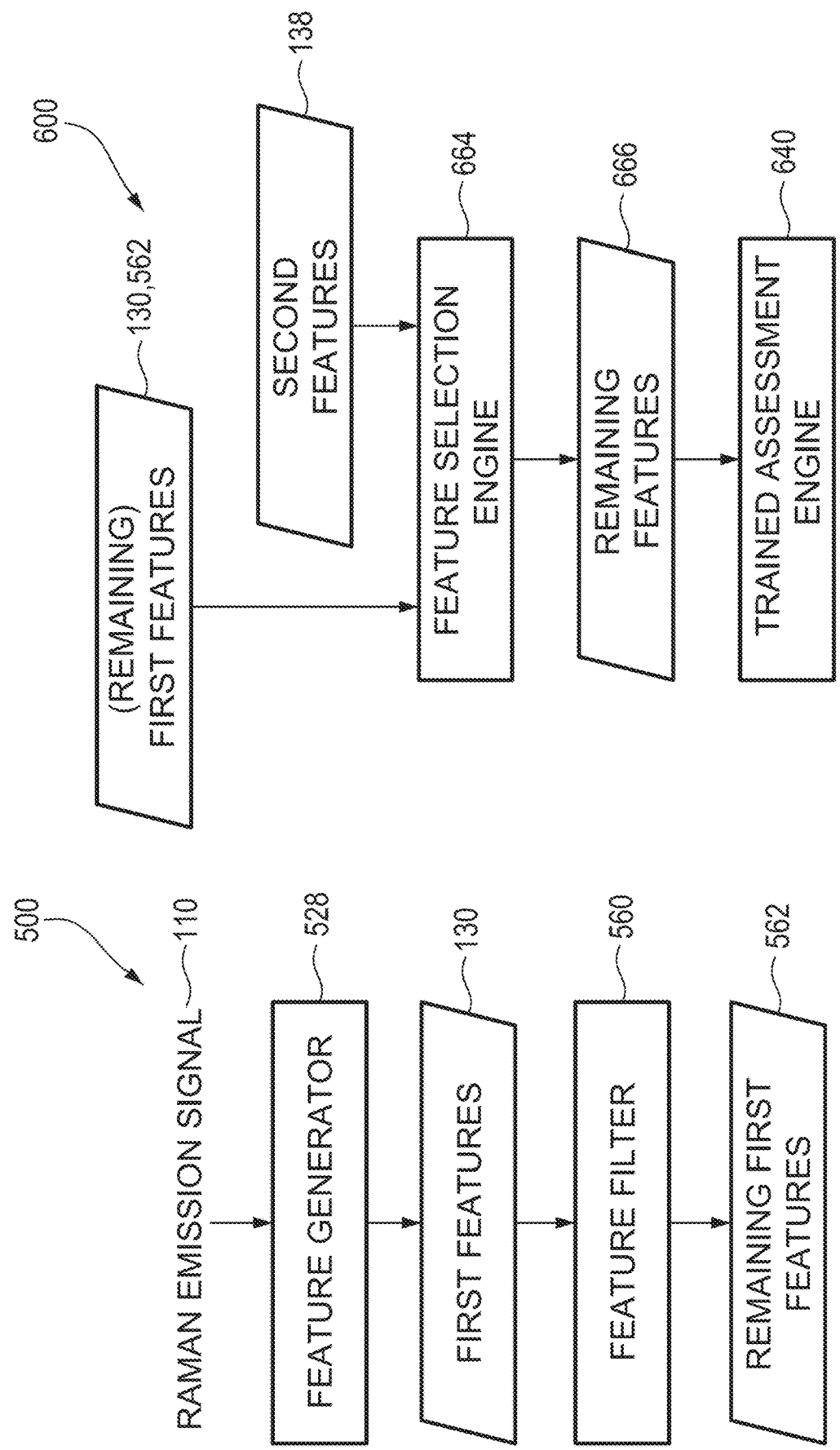

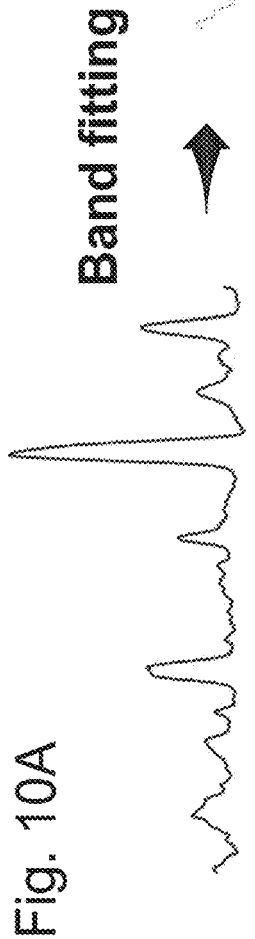
Fig. 10A
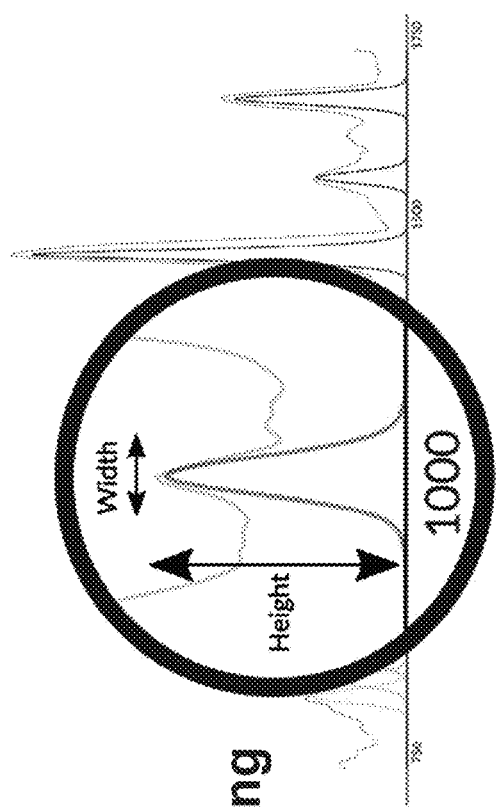
Band fitting
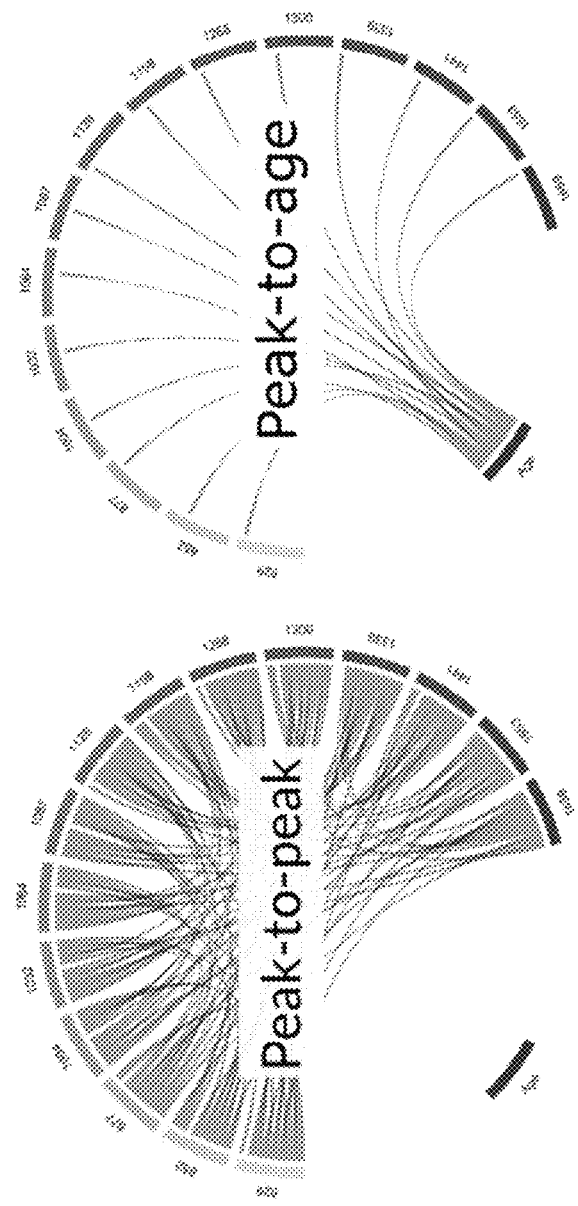
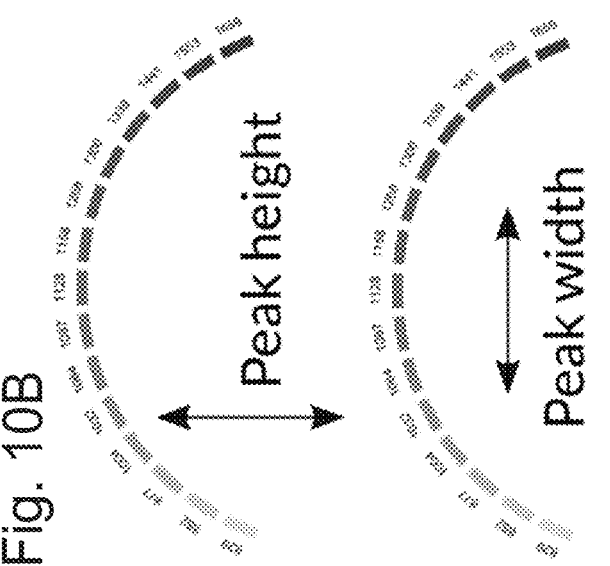
Fig. 10B

METHODS AND SYSTEMS FOR ASSESSING A PHENOTYPE OF A BIOLOGICAL TISSUE OF A PATIENT USING RAMAN SPECTROSCOPY

REFERENCE TO RELATED APPLICATIONS

This is a U.S. National Stage of International Application PCT/IB2020/055252, filed Jun. 3, 2020, which claims the benefit of priority of U.S. Provisional Application 62/856,181, filed Jun. 3, 2019.

BACKGROUND

Raman spectroscopy is a spectroscopic technique which can be used to characterize atoms or molecules of a biological tissue of a patient. In this technique, the biological tissue, or a portion thereof, is illuminated with a Raman excitation signal, generally comprising monochromatic photons, which excites vibrational, rotational, and/or other low-frequency modes of the atoms or molecules of the biological tissue in a manner which causes them to scatter photons having a different energy level than those of the incident monochromatic photons. The scattered photons are generally referred to as a "Raman emission signal." The shift(s) in the energy level between the incident photons and the scattered photons gives signature information which can be used to characterize the atoms or molecules of the biological tissue.

It is known that Raman spectroscopy can be used in medical fields to determine whether a biological tissue contains healthy or unhealthy cells, based on the respective signature information of such cells. A technique often referred to as "single-point Raman spectroscopy" involves optical probes to interrogate a point of the sample, and collect the Raman emission signal therefrom to determine whether, at that point, the biological tissue contains healthy or unhealthy cells. To obtain information concerning different portions of the biological tissue, the optical probe is manipulated to interrogate, sequentially, each one of the portions of the biological tissue.

Although existing Raman spectroscopy systems have been satisfactory to a certain degree, there remains room for improvement, especially in reducing the time required for a phenotype of a portion of the biological tissue to be assessed based on such Raman emission signal, and/or increasing the accuracy of the assessed phenotype.

SUMMARY

Although some attempts to using artificial intelligence (AI) have been made in the field of Raman spectroscopy, there remains challenges in suitably extracting features from the Raman emission signal or spectrum that are to be fed to an AI-trained engine. It was found that feeding unsuitable data (e.g., wrong data, too much data) to existing AI-trained engines could impede the speed at which phenotypes could be assessed and, more importantly, could also impede the accuracy of such assessments. As suitably selecting the right features from the Raman emission signal or spectrum for a particular biological tissue can be time-costly and require domain-expertise, selecting such features is still perceived as a bottleneck in improving such AI engines in terms of computational loads and performances.

The inventors found that the existing AI-trained engines do not account for clinical parameters associated to the patient to which belong the biological tissue requiring phenotype assessment. Moreover, the existing AI-trained engines do not account for strongly correlated features of the Raman emission signal or spectrum. Accordingly, existing AI-trained engines may not assess phenotypes in a way that is compatible with what is sought in the operating room.

In an aspect, there is described a phenotype assessment system for assessing a phenotype of a biological tissue of a patient which can alleviate at least some of the above-mentioned drawbacks. The phenotype assessment system has a Raman spectroscopy system receiving a Raman emission signal indicative of Raman emission from a portion of the biological tissue. Using a feature generator, a value of a first feature is determined based on the received Raman emission signal. Upon receiving a value of a clinical parameter (e.g., age, gender) associated to the patient, an interactor generates a value of a second feature by interacting (e.g., multiplying) the value of the first feature with the value of the clinical parameter. Using a trained assessment engine, the phenotype of the biological tissue is then assessed based on the values of the first and second features, the result of which can be outputted in the form of a signal.

In another aspect, there is described a phenotype assessment system for assessing a phenotype of a biological tissue of a patient which can alleviate at least some of the above-mentioned drawbacks. The phenotype assessment system has a Raman spectroscopy system receiving a Raman emission signal indicative of Raman emission from a portion of the biological tissue. Using a feature generator, values of a plurality of first features are determined based on the received Raman emission signal. An interactor generates a value of a second feature by interacting (e.g., multiplying) the value of one of the plurality of first features with the value of one of the remaining first features. Still in this aspect, the phenotype of the biological tissue is then assessed, using a trained assessment engine, based on the values of the first and second features.

In any of these aspects, the first feature can be indicative of an intensity of a peak of the Raman emission signal. For instance, in such embodiments, the feature generator can be provided in the form of an optical intensity detector measuring intensity at a predetermined wavelength or frequency corresponding to the peak of the Raman emission signal. In some other embodiments, the first feature can be indicative of a spectral width at half-maximum of the peak of the Raman emission signal. In these embodiments, the feature generator can include a spectrometer receiving the Raman emission signal and measuring spectrally spaced-apart intensity values of the signal, and a computing device determining the value of the first feature based on the received intensity values.

In accordance with another aspect, there is provided a method of assessing a phenotype of a biological tissue of a patient, the method comprising: receiving a Raman emission signal indicative of Raman emission of a portion of said biological tissue; using a feature generator, determining a value of a first feature based on said received Raman emission signal; using a computing device, receiving a value of a clinical parameter associated to the patient; generating a value of a second feature by interacting said value of said first feature with said value of said clinical parameter; using a trained assessment engine, assessing the phenotype of the biological tissue based on at least said value of said second feature; and outputting a signal based on said assessment.

In accordance with another aspect, there is provided a phenotype assessment system for assessing a phenotype of a biological tissue of a patient, the phenotype assessment system comprising: a Raman spectroscopy system receiving a Raman emission signal indicative of Raman emission from a portion of said biological tissue; using a feature generator, determining a value of a first feature based on said received Raman emission signal; using a computing device having a processor and a memory having stored thereon instructions which when executed by the processor perform the steps of: receiving a value of a clinical parameter associated to the patient; using an interactor, generating a value of a second feature by interacting said value of said first feature with said value of said clinical parameter; assessing, using a trained assessment engine, the phenotype of the biological tissue based on at least said value of said second feature; and outputting a signal based on said assessment.

In accordance with another aspect, there is provided a method of assessing a phenotype of a biological tissue of a patient, the method comprising: receiving a Raman emission signal indicative of Raman emission of a portion of said biological tissue; using a feature generator, determining values of a plurality of first features based on said received Raman emission signal; using a computing device, generating a value of a second feature by interacting the value of at least one of said plurality of first features with the value of a remaining one of said plurality of first features; using a trained assessment engine, assessing the phenotype of the biological tissue based on at least said value of said second feature; and outputting a signal based on said assessment.

In accordance with another aspect, there is provided a phenotype assessment system for assessing a phenotype of a biological tissue of a patient, the phenotype assessment system comprising: a Raman spectroscopy system receiving a Raman emission signal indicative of Raman emission from a portion of said biological tissue; using a feature generator, determining values of a plurality of first feature based on said received Raman emission signal; using a computing device having a processor and a memory having stored thereon instructions which when executed by the processor perform the steps of: using an interactor, generating a value of a second feature by interacting the value of at least one of said plurality of first features with the value of a remaining one of said plurality of first features; assessing, using a trained assessment engine, the phenotype of the biological tissue based on at least said value of said second feature; and outputting a signal based on said assessment.

Many further features and combinations thereof concerning the present improvements will appear to those skilled in the art following a reading of the instant disclosure.

DESCRIPTION OF THE FIGURES

In the figures,

FIGS. 1A to 1E show an exemplary implementation of a method of assessing a phenotype of a portion of a biological tissue using a fiber-optic Raman probe, in accordance with one or more embodiments;

FIG. 3 is a graph showing intensity as function of wavelength for an example of a Raman emission signal measured using the fiber-optic Raman probe of FIG. 1, showing examples of first features, in accordance with one or more embodiments;

FIG. 7 is a schematic view of an example portion of a phenotype assessment system, showing a feature filter, in accordance with one or more embodiments;

FIG. 8 is a schematic view of an example portion of a phenotype assessment system, showing an example of a feature selection engine, in accordance with one or more embodiments;

FIG. 10A shows an exemplary implementation of a band fitting algorithm associating values of different first features for a Raman spectrum, in accordance with one or more embodiments;

FIG. 10B is a schematic illustration showing different first features, including intensity and width at half maximum obtained using the bead fitting algorithm of FIG. 10A, and second features including intensity-to-intensity and intensity-to-age interactions, in accordance with one or more embodiments;

DETAILED DESCRIPTION

Figure 2:
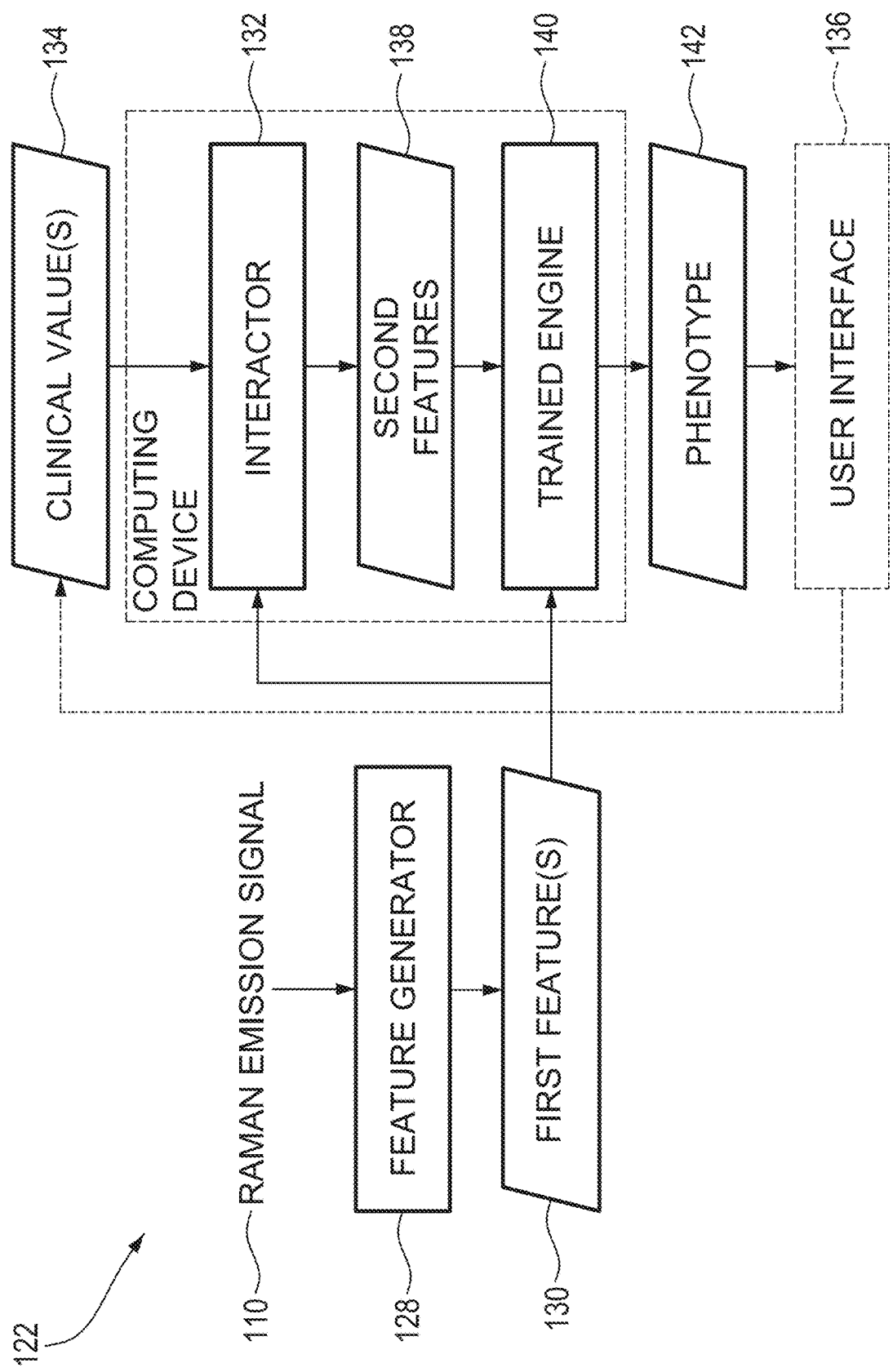
FIG. 2 is a schematic view of an example of a phenotype assessment system, incorporating a feature generator, an interactor and a trained assessment engine, in accordance with one or more embodiments.

FIGS. 1A through 1E show an example of a method of assessing a phenotype of one or more portions of a biological tissue 100 using a Raman spectroscopy system 102. As depicted in FIG. 1A, the biological tissue 100 can have more than one portion to assess. In this example, the biological tissue 100 has a first portion 104a and a second portion 104b spaced-apart from the first portion 104a. The method aims at assessing a phenotype of at least the first portion 104a of the biological tissue 100.

FIG. 1B shows a portion of the Raman spectroscopy system 102 having a Raman excitation source (not shown) emitting a Raman excitation signal 106. It is intended that the Raman excitation signal 106 typically has monochromatic photons, which collectively excite vibrational, rotational, and/or other low-frequency modes of the atoms or molecules 108 of the first portion 104a of the biological tissue 100 in a manner which causes them to scatter photons having a different energy level than those of the incident monochromatic photons. The scattered photons constitute the Raman emission signal 110. The spectral content of the Raman excitation signal 110 can depend on the embodiment. However, in some embodiments, the Raman excitation signal 110 comprises monochromatic photons at a given wavelength $\lambda 0$. Examples of such wavelength can include, but not limited to, 671 nm, 785 nm, 830 nm and 1064 nm.

In this example, the Raman spectroscopy system 102 has an example of a fiber-optic Raman probe 112. The fiber-optic Raman probe 112 receives the Raman excitation signal 106 from the Raman excitation source and propagates the received Raman excitation signal 106 towards the portion 104a of the biological tissue 100 which a phenotype assessment is sought. In the illustrated embodiment, the fiber-optic Raman probe 112 can include a central fiber-optic cable 114 along which the Raman excitation signal 106 is propagated, and one or more peripheral fiber-optic cables 116 around the central fiber-optical cable 114 for collecting the Raman emission signal 106 scattering from the portion 104a of the biological tissue 100. Examples of such fiber-optic probes are described in International Application Publication Nos. PCT/CA2015/050288, PCT/CA2018/051140, PCT/SG2013/000273 and PCT/CA2004/002040 and in U.S. Provisional Application Ser. No. 62/746,306, the contents of which are hereby incorporated by reference. However, other embodiments of the fiber-optic Raman probe can be provided equivalently. In alternate embodiments, the Raman spectroscopy system rather involves free-space optical components.

FIG. 1C shows an example of a Raman emission spectrum 110', including spectrally spaced-apart peaks 120, showing shift(s) in the energy level between the incident photons and the scattered photons that carry the signature information which can be used to characterize the atoms or molecules 108 of the first portion 104a of the biological tissue 100. As shown at FIG. 1D, a phenotype assessment system 122 is used to assess the phenotype of the first portion 104a of the biological tissue 100 at least based on the Raman emission signal 110.

As can be understood, the fiber-optic Raman probe 112 can interrogate a plurality of other portions of the biological tissue 100, including the first and second portions 104a, 104b, the results of which can be plotted in the form of a phenotype map 124, such as the one shown in FIG. 1E. As shown, in this example, the first portion 104a has a first phenotype 126a assessed to be healthy whereas the second portion 104b has a second phenotype 126b assessed to be unhealthy.

FIG. 2 shows an example of the phenotype assessment system 122 shown in FIG. 1. The phenotype assessment system 122 has a feature generator 128 which, based on the Raman emission signal 110, determine value(s) of one or more first feature(s) 130. Each first feature 130 represents a given portion or characteristic of interest of the Raman emission signal 110.

Examples of such first features 130 are provided in the Raman emission spectrum 110' best shown in FIG. 3. For instance, one example first feature 130 can be the intensity I of the Raman emission signal 110 at a peak 120 near a first wavelength $\lambda 1$, i.e., $I(\lambda 1)$. Similarly, the intensity I near wavelengths $\lambda i$, with i being an integer ranging from 2 to 15, can be other examples of first features 130. Another example first feature 130 can be the spectral width $\Delta\lambda$ taken at half-maximum for the peak 120 near the first wavelength $\lambda 1$, i.e., $\Delta\lambda 1$. Similarly, the spectral width $\Delta\lambda i$ near wavelengths $\lambda i$, with i being an integer ranging from 2 to 15, can be other examples of first features 130. As can be appreciated, in the illustrated Raman emission spectrum 110', there can be thirty of such first features 130, with fifteen first features relating to peak intensities Ii and the remaining fifteen first feature 130 relating to spectral widths $\Delta\lambda i$. Other examples of first features include, but are not limited to, peak spacings, widths at a given percentage of the maximum, type of peak shape, peak distance from expected location, moments describing shape of peak such as skewness, kurtosis and/or hypertailedness, and the like.

In this embodiment, the phenotype assessment system 122 has an interactor 132 receiving value(s) Ci of one or more clinical parameters 134 associated to the patient from which the biological tissue 100 originates, with i being a positive integer. In some embodiments, the clinical parameter 132 is associated to an age of the patient. The clinical parameter 132 can be associated to a gender of the patient. In some embodiments, there are more than one clinical parameters 132. One of the clinical parameters 132 may be associated to the age of the patient whereas another one of the clinical parameters 132 may be associated to the gender of the patient. Examples of such clinical parameters 132 can include, but are not limited to, age, gender, race, genetic mutations, co-morbid diseases (e.g., neurodegenerative diseases, vascular pathologies, epilepsy), imaging findings (e.g., necrosis, calcifications, bleeding, high vascularization), cancer history (e.g., recurrent cancer, previous surgical operation, radiotherapy, chemotherapy), and the like.

In some embodiments, the interactor 132 receives the value(s) Ci of the clinical parameter(s) 134 from a memory system, remote network, a remote computing system and/or a combination thereof. In some other embodiments, the phenotype assessment system 122 has a user interface 136 through which the value(s) Ci of the clinical parameter(s) 134 can be inputted manually.

The interactor 132 also receives the value(s) of the first feature(s) 130 from the feature generator 128. Once received, the interactor 132 generates value(s) of one or more second feature(s) 138 by interacting the value(s) of the first feature(s) 130 with the value(s) Ci of the clinical parameter(s) 134. The interaction can include a multiplication, division, addition, subtraction, maximum, minimum, any combination thereof, and/or any other arithmetic operating between the value(s) of the first feature(s) 130 and the value(s) Ci of the clinical parameter(s) 134. Higher-order interactions could be included as well, including combination of arithmetic operations between an arbitrary number of values(s) of the first feature(s) and/or any number of value(s) of clinical parameter(s).

As shown, the phenotype assessment system 122 has a trained assessment engine 140 receiving the value(s) of the first feature(s) 130 directly from the feature generator 128 and/or indirectly from the interactor 132, and the value(s) of the second feature(s) 138 from the interactor 132. Once the values of the first and second features 130, 138 are received, the trained assessment engine 140 assesses the phenotype of the biological tissue 100 based on the received values, after which a signal indicative of the assessed phenotype 142 can be outputted. In some embodiments, the trained assessment engine 140 assesses the phenotype of the biological tissue 100 based on the value(s) of the second feature(s). In some other embodiments, the trained assessment engine 140 assesses the phenotype of the biological tissue 100 based on the values of the first and second features.

In some embodiments, the user interface 136 displays the assessed phenotype 142 of the biological tissue 100 based on the signal outputted by the trained assessment engine 140. For instance, when the biological tissue 100 is assessed for oncologic purposes, the displayed phenotype 142 can be one of "cancerous" or "healthy," thus helping the surgeon remove only portions of the biological tissue 100 which are assessed to be cancerous by the phenotype assessment system 122. As discussed, the value(s) Ci of the clinical parameter(s) 134 can be inputted in the phenotype assessment system 122 via the user interface 136 which can also display the assessed phenotype 142 of the portion of the biological tissue 100 thereafter.

Figure 5:
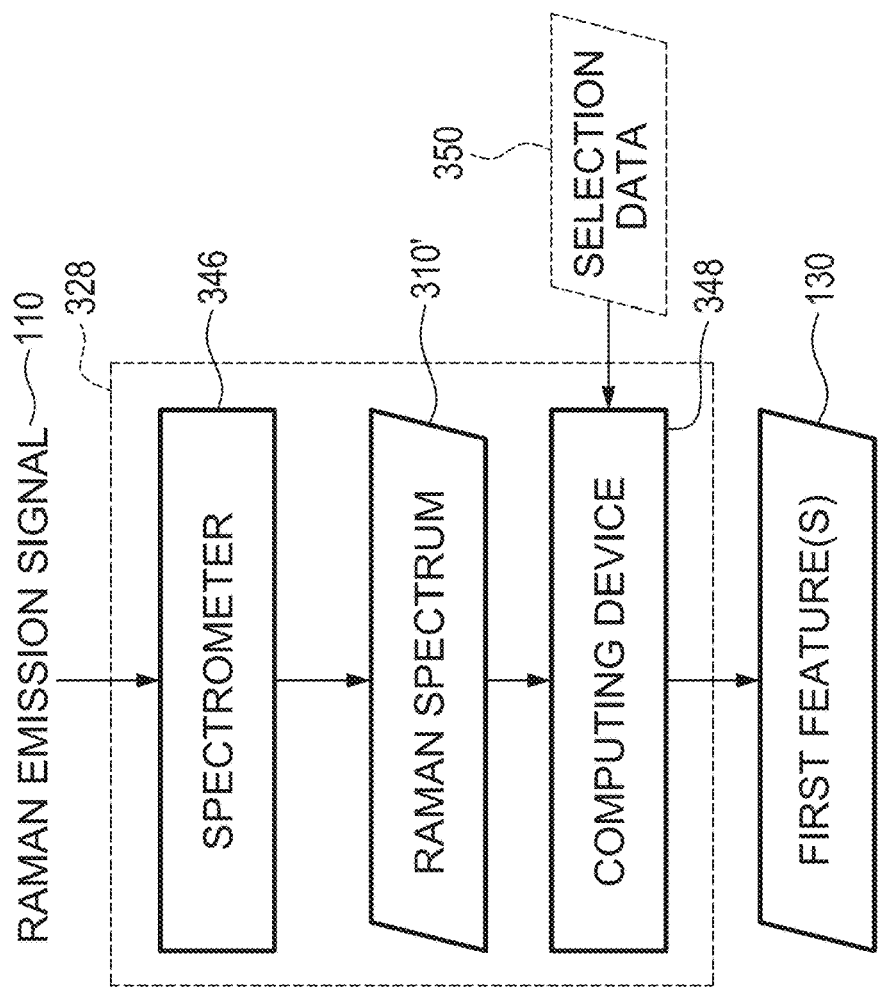
FIG. 5 is a schematic view of another example of a computing device of the feature generator of FIG. 2, shown with a spectrometer and a computing device, in accordance with one or more embodiments.
Figure 4:
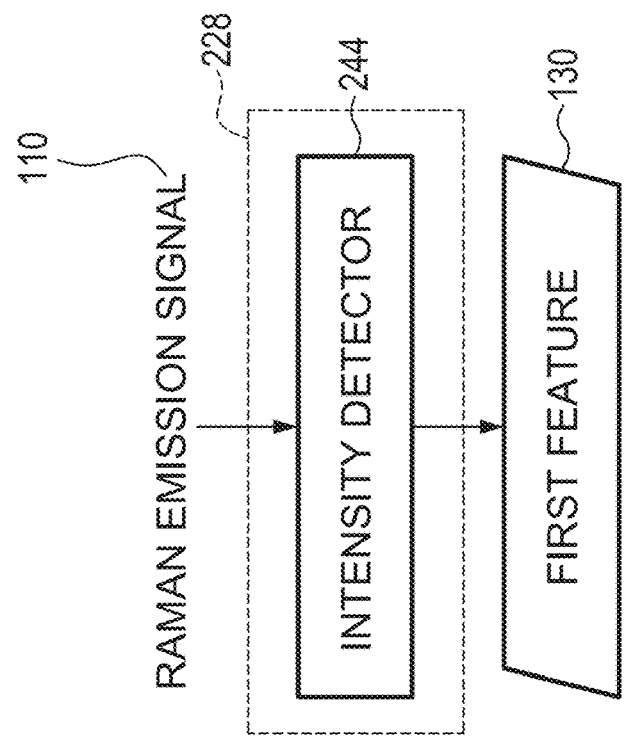
FIG. 4 is a schematic view of an example of a computing device of the feature generator of FIG. 2, shown with an intensity detector, in accordance with one or more embodiments.

Different embodiments of the feature generator 128 are possible, as shown in FIGS. 4 and 5. FIG. 4 shows an example of a feature generator 228. In this embodiment, the first feature 130 represents an intensity peak at a given wavelength $\lambda 1$ of the Raman emission signal 110. As such, in this embodiment, the feature generator 228 can include an intensity detector 244 which is configured to determine values of the intensity peak around the given wavelength $\lambda 1$. For instance, the intensity detector 244 can have one or more optical filters (not shown) to filter out any portion of the Raman emission signal 110 which is away from the given wavelength $\lambda 1$ and letting pass the portion of the Raman emission signal 110 around the given wavelength $\lambda 1$.

FIG. 5 shows an example of a more sophisticated feature generator 328. In this embodiment, the feature generator 328 has a spectrometer 346 receiving the Raman emission signal 110 and generating a Raman emission spectrum 110', i.e., a series of data indicative of intensity values associated to different wavelength or frequency values. In such embodiments, a computing device 348 can be provided to receive the Raman emission spectrum 110' discussed above and determine the values of the first feature 130 based on the Raman emission spectrum 110'. In some embodiments, the computing device 348 can receive selection data 350 indicative of a selection of first feature(s) 130 of the Raman emission spectrum which are of interest, and determine value of the so-selected first features 130 based on the received selection data 350.

Referring back to FIG. 3, it in intended that although the feature generator 328 can determine thirty values for the thirty first features 130, the feature generator 328 can be configured to determine values for only some of these thirty first features 130. In some embodiments, the feature generator 328 can determine the values for a plurality of selected first features 130 based on the selection data 350 which indicate a selection of predetermined ones of the first features 130 from the Raman emission signal 110. For instance, the predetermined first features 130 can only include six of the thirty first features 130, e.g., $I(\lambda 3)$, $I(\lambda 5)$, $I(\lambda 7)$, $\Delta\lambda 3$, $\Delta\lambda 9$ and $\Delta\lambda 11$. The number of first features 130 which values are determined by the feature generator 328 can depend on the type of biological tissue 100, on the type of tissue phenotype that is to be assessed, and/or on the Raman excitation signal 110 used. As can be understood, the greater the number of first features 130, the more the assessment performed by the trained assessment engine 140 can be long and computationally cumbersome. Also, some first features 130 can be more phenotype-indicative than others. Accordingly, some of the first features 130 of the Raman emission signal 110 can be advantageously selected over other first features 130 that can be neglected in the assessment, depending on the application. For instance, in embodiments where the biological phenotype is assessed to determine whether it is cancerous or healthy, the selected first features can include $I(\lambda 3)$, $I(\lambda 5)$, $I(\lambda 7)$, $\Delta\lambda 3$, $\Delta\lambda 9$ and $\Delta\lambda 11$: In some embodiments, the first features can include intensities at peaks near 1659 $cm^{-1}$, 852 $cm^{-1}$, 877 $cm^{-1}$, 1553 $cm^{-1}$, 1004 $cm^{-1}$, and 1339 $cm^{-1}$, and spectral widths at half maximum at peaks near 1004 $cm^{-1}$, 1553 $cm^{-1}$, 1339 $cm^{-1}$, and 852 $cm^{-1}$.

| Selected first features | Value |
| --- | --- |
| $I(\lambda 3)$ | 50 |
| $I(\lambda 5)$ | 50 |
| $I(\lambda 7)$ | 110 |
| $\Delta\lambda 3$ | 3 |
| $\Delta\lambda 9$ | 4 |
| $\Delta\lambda 11$ | 2 |

Referring back to FIG. 2, and with reference to the selected first features $I(\lambda 3)$, $I(\lambda 5)$, $I(\lambda 7)$, $\Delta\lambda 3$, $\Delta\lambda 9$ and $\Delta\lambda 11$ identified above, and in embodiments where the value C1 of the clinical parameter 134 relates to the age of the patient (e.g., 50 years old), the interactor 132 can generate values corresponding to $I(\lambda 3) \times C1$, $I(\lambda 5) \times C1$, $I(\lambda 7) \times C1$, $\Delta\lambda 3 \times C1$, $\Delta\lambda 9 \times C1$ and $\Delta\lambda 11 \times C1$:

| Selected first features | Value | Second features | Value |
| --- | --- | --- | --- |
| $I(\lambda 3)$ | 50 | $(\lambda 3) \times C1$ | 2500 |
| $I(\lambda 5)$ | 50 | $I(\lambda 5) \times C1$ | 2500 |
| $I(\lambda 7)$ | 110 | $I(\lambda 7) \times C1$ | 5500 |
| $\Delta\lambda 3$ | 3 | $\Delta\lambda 3 \times C1$ | 150 |
| $\Delta\lambda 9$ | 4 | $\Delta\lambda 9 \times C1$ | 200 |
| $\Delta\lambda 11$ | 2 | $\Delta\lambda 11 \times C1$ | 100 |

In such a case, the trained assessment engine 140 may assess the phenotype of the portion 104a of the biological tissue 100 based on the values of the first features $I(\lambda 3)$, $I(\lambda 5)$, $I(\lambda 7)$, $\Delta\lambda 3$, $\Delta\lambda 9$ and $\Delta\lambda 11$ and on the values of the second features $I(\lambda 3) \times C1$, $I(\lambda 5) \times C1$, $I(\lambda 7) \times C1$, $\Delta\lambda 3 \times C1$, $\Delta\lambda 9 \times C1$ and $\Delta\lambda 11 \times C1$. Other examples may apply, depending on the embodiment.

Figure 5A:
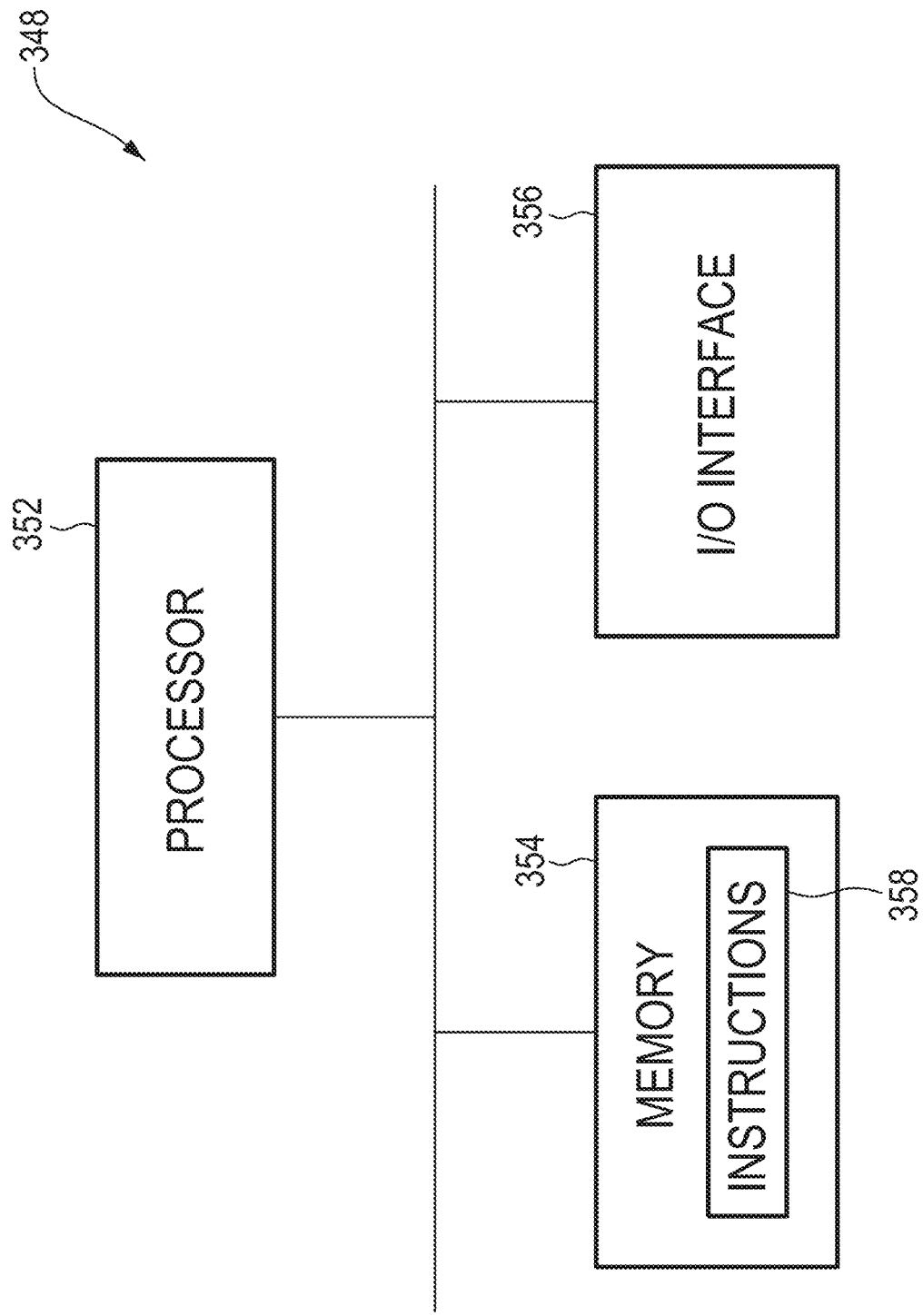
FIG. 5A is a schematic view of an example of the computing device of FIG. 5, in accordance with one or more embodiments.

FIG. 5A is a schematic view of an example of the computing device 348 of the feature generator 328 of FIG. 5. The computing device 348 can be provided as a combination of hardware and software components, an example of which is described with reference to FIG. 5A.

Referring to FIG. 5A, the computing device 348 can have a processor 352, a memory 354, and I/O interface 356. Instructions 358 for determining the value(s) of the first features 130 can be stored on the memory 354 and accessible by the processor 352.

The processor 352 can be, for example, a general-purpose microprocessor or microcontroller, a digital signal processing (DSP) processor, an integrated circuit, a field programmable gate array (FPGA), a reconfigurable processor, a programmable read-only memory (PROM), or any combination thereof.

The memory 354 can include a suitable combination of any type of computer-readable memory that is located either internally or externally such as, for example, random-access memory (RAM), read-only memory (ROM), compact disc read-only memory (CDROM), electro-optical memory, magneto-optical memory, erasable programmable read-only memory (EPROM), and electrically-erasable programmable read-only memory (EEPROM), Ferroelectric RAM (FRAM) or the like.

Each I/O interface 356 enables the computing device 348 to interconnect with one or more input devices, such as the spectrometer 346, or with one or more output devices such as the interactor 132, the trained assessment engine 140 and/or the user interface 136.

Each I/O interface 356 enables the computing device 348 to communicate with other components, to exchange data with other components, to access and connect to network resources, to serve applications, and perform other computing applications by connecting to a network (or multiple networks) capable of carrying data including the Internet, Ethernet, plain old telephone service (POTS) line, public switch telephone network (PSTN), integrated services digital network (ISDN), digital subscriber line (DSL), coaxial cable, fiber optics, satellite, mobile, wireless (e.g., Wi-Fi, WiMAX), SS7 signaling network, fixed line, local area network, wide area network, and others, including any combination of these.

The computing device 348 described above is meant to be an example only. Other suitable embodiments of the computing device 348 can also be provided, as it will be apparent to the skilled reader. For instance, both the interactor 132 and the trained assessment engine 140 can be implemented as part of the computing device 348. In some embodiments, the interactor 132 and/or the trained assessment engine 140 are/is implemented in the form of a computing device similar to the computing device 348.

In another aspect, the value(s) of the clinical parameter(s) may be optional. For instance, in some embodiments, the second features can originate by an interaction between some of the value(s) of the first feature(s) to some other value(s) of the first feature(s), in which case the value(s) of the clinical parameter(s) can be omitted.

Figure 6:
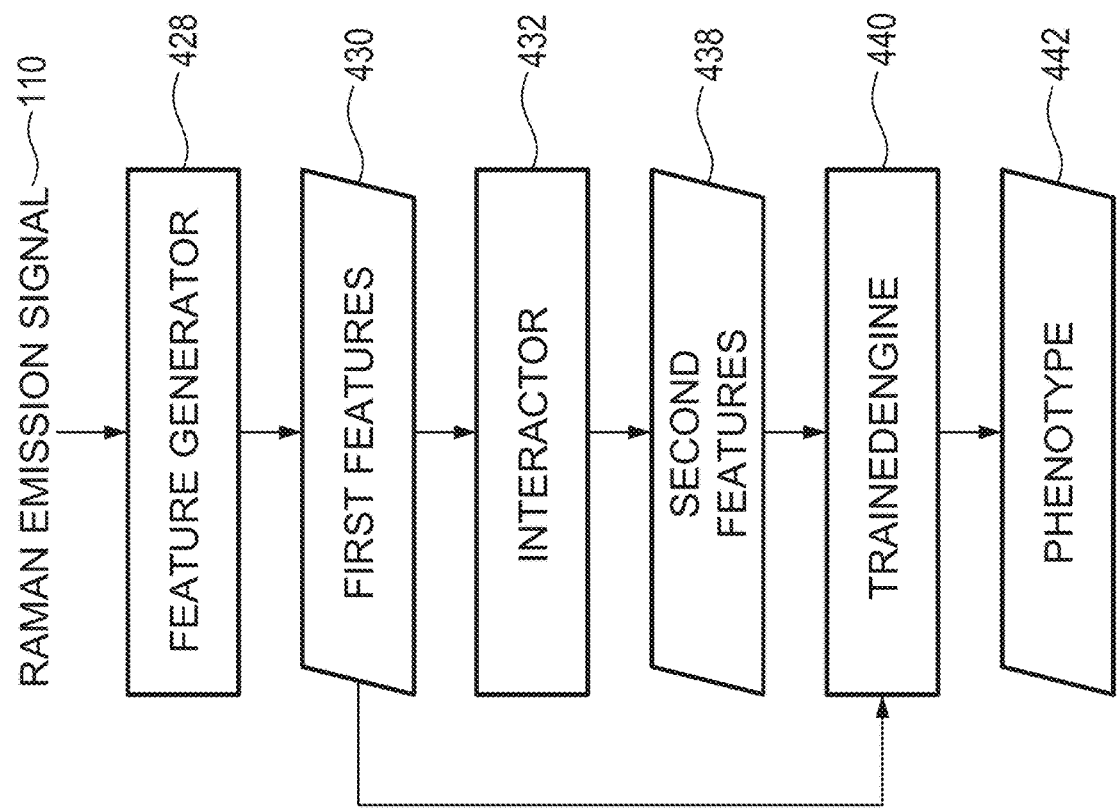
FIG. 6 is a schematic view of another example of a phenotype assessment system, in accordance with one or more embodiments.

FIG. 6 shows another example of a phenotype assessment system 422. As depicted, the feature generator 428 receives the Raman emission signal 110, and determines values of a plurality of first features 430 such as those discussed above with reference to the phenotype assessment system 122 of FIG. 2. The phenotype assessment system 422 has an interactor 432 which receives the values of the first features 430 and generates values of a plurality of second features 438 by interacting the values of some or all of the first features 430 with the values of one or more of the remaining first features 430.

The phenotype assessment system 422 has a trained assessment engine 440 receiving the values of the first features 430 directly from the feature generator 430 or indirectly from the interactor 432, and the values of the second features 438 from the interactor 432. Once the values of the first and second features 430, 438 are received, the trained assessment engine 440 assesses the phenotype 442 of the biological tissue 100 based on the received values, after which a signal indicative of the assessed phenotype 442 can be outputted.

With reference to the example above, in which the first features 430 are features $I(\lambda 3)$, $I(\lambda 5)$, $I(\lambda 7)$, $\Delta\lambda 3$, $\Delta\lambda 9$ and $\Delta\lambda 11$, the second features may result from an interaction between these first features and the first feature $I(\lambda 3)$, for instance. In this case, the second features may include $I(\lambda 3)\times I(\lambda 3)$, $I(\lambda 5)\times I(\lambda 3)$, $I(\lambda 7)\times I(\lambda 3)$, $\Delta\lambda 3\times I(\lambda 3)$, $\Delta\lambda 9\times I(\lambda 3)$ and $\Delta\lambda 11\times I(\lambda 3)$.

| Selected first features | Value | Second features | Value |
| --- | --- | --- | --- |
| $I(\lambda 3)$ | 50 | $I(\lambda 3) \times I(\lambda 3)$ | 2500 |
| $I(\lambda 5)$ | 50 | $I(\lambda 5) \times I(\lambda 3)$ | 2500 |
| $I(\lambda 7)$ | 110 | $I(\lambda 7) \times I(\lambda 3)$ | 5500 |
| $\Delta\lambda 3$ | 3 | $\Delta\lambda 3 \times I(\lambda 3)$ | 150 |
| $\Delta\lambda 9$ | 4 | $\Delta\lambda 9 \times I(\lambda 3)$ | 200 |
| $\Delta\lambda 11$ | 2 | $\Delta\lambda 11 \times I(\lambda 3)$ | 100 |

As will be discussed below, the interaction of the value(s) of the first features with the value(s) of the clinical parameters and/or other value(s) of the first features can help a properly trained assessment engine to assess the phenotype of the first portion with reduced computational delays and/or increased accuracy.

FIG. 7 shows a portion of a phenotype assessment system 500, in accordance with an embodiment. As depicted, the phenotype assessment system 500 has a feature generator 528 receiving a Raman emission signal 110 and determining values of a plurality of first features 130 based on the received Raman emission signal 110. In this embodiment, the phenotype assessment system 500 has a feature filter 560 which is configured for filtering out some of the received first features 130 and for outputting one or more remaining first features 562. The feature filter 560 is configured to filter out at least some of the first features which are known to have an insufficient correlation with the phenotype to be assessed. In contrast, the remaining first features 562 outputted by the feature filter 560 are known to have a sufficient correlation with the phenotype to be assessed. Accordingly, using only the remaining first features 562 outputted from the feature filter 560, the phenotype assessment system 500 can be more efficient in the assessment of the phenotype of the portion of the biological sample 100. The feature filter 560 can be separate from the feature generator 528 in some embodiments whereas the feature filter 560 can be integrated to the feature generator 528 in some embodiments (see FIG. 5). The feature filter 560 can differ depending on the type of phenotype that are expected, on the type of biological tissue to assess and/or other biological or clinical factors. An example of the feature filter 560 is provided below with reference to Example 1.

FIG. 8 shows a portion of a phenotype assessment system 600, in accordance with an embodiment. As shown, the phenotype assessment system 600 has a feature selection engine 664 which receives the first features 130 or the remaining first features 562 discussed with reference to FIG. 7 and the second features 138, and selects some of the features 130, 562 and 138 as the features to be inputted in the trained assessment engine 640. As can be appreciated, the feature selection engine 664, when used concurrently with a feature filter such as the feature filter 560 of FIG. 7 or alone, can allow the phenotype assessment system 600 to input remaining features 666 to the trained assessment engine 640. In this way, the total number of features inputted in the trained assessment engine 640 can be lowered, which in turn can reduce the computational load imparted on the trained assessment engine 640. Similarly to the feature filter 560, the feature selection engine 664 is configured to filter out at least some of the features 130, 562 and 138 which are known to have an insufficient correlation with the phenotype to be assessed. In contrast, the remaining features 666 outputted by the feature selection engine 664 are known to have a sufficient correlation with the phenotype to be assessed. In some embodiments, a satisfactory number of remaining features 666 can range between 10 and 100, preferably between 15 and 50, and most preferably between 20 and 30. An example of the feature selection engine 664 is provided below with reference to Example 1.

It is intended that the number of remaining features 666 can depend heavily on the number of observations and/or on the number of Raman spectra-tissue samples that are available. Generally, the phenotype assessment system can require the number of remaining features 666 to be about ten times the number of observations. As such, in an example, for a dataset comprising 250 Raman spectra, 25 remaining features 666 could be satisfactory. Depending on the type of engine training on these features, the remaining features 666 could, however, be more numerous in some other embodiments.

The feature selection engine 664 can involve a Bayesian filter in some embodiments. However, in some other embodiments, the feature selection engine 664 can involve comparing correlation between features and prediction such as Fisher score-based feature selection, pointwise mutual information-based feature selection, relief-based feature selection; comparing accuracy gain and/or loss after including or excluding the feature from a predictive model such as stepwise feature elimination-based feature selection, stepwise feature addition-based feature selection, random forest-based feature selection; and embedded methods using optimisation penalisation to favor important features such as LASSO regression, ridge regression, bootstrap LASSO, elastic net, support vector machine with L1 penalization, Bayesian LASSO and/or any combination thereof.

Figure 8A:
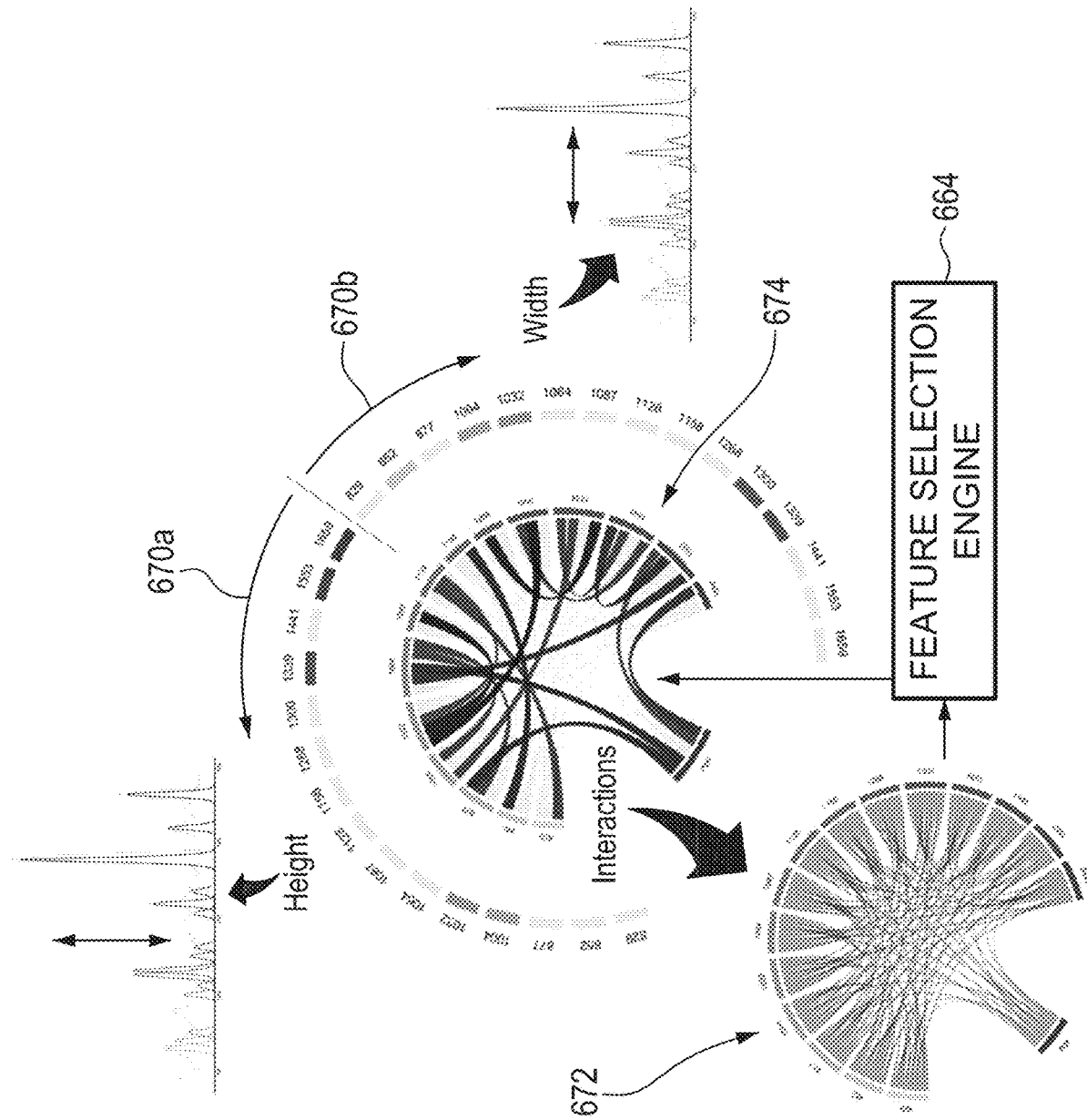
FIG. 8A is a schematic illustration showing selected ones of a plurality of first and second features as selected by the feature selection engine of FIG. 8, in accordance with one or more embodiments.

FIG. 8A shows a schematic example of the selection performed by the feature selection engine 664. In this example, the first features includes the a first set 670a of first features indicative of peak intensities including I(829 nm), I(852 nm), I(877 nm), I(1004 nm), I(1032 nm), I(1064 nm), I(1087 nm), I(1128 nm), I(1158 nm), I(1268 nm), I(1300 nm), I(1339 nm), I(1441 nm), I(1553 nm) and a second set 670b of first features indicative of spectral widths at half-maximum including I(1659 nm), $\Delta\lambda(829$ nm), $\Delta\lambda(852$ nm), $\Delta\lambda(877$ nm), $\Delta\lambda(1004$ nm), $\Delta\lambda(1032$ nm), $\Delta\lambda(1064$ nm), $\Delta\lambda(1087$ nm), $\Delta\lambda(1128$ nm), $\Delta\lambda(1158$ nm), $\Delta\lambda(1268$ nm), $\Delta\lambda(1300$ nm), $\Delta\lambda(1339$ nm), $\Delta\lambda(1441$ nm), $\Delta\lambda(1553$ nm), $\Delta\lambda(1659$ nm). When all the first features of the first and second sets 670a and 670b are interacted with a value C of a clinical parameter, in this case the clinical parameter is the age of the patient, a set 672 of second features are obtained. However, as shown, once the first features of the first and second sets 670a, 670b and the set 672 of second features are selected using the feature selection engine 664, a set 674 of remaining features remains.

Indeed, as mentioned above, the trained assessment engines 140, 440 and 640 are trained using supervised learning. In such supervised learning, each training image in the set of training images may be associated with a label while training. Supervised machine learning engines can be based on Artificial Neural Networks (ANN), Support Vector Machines (SVM), capsule-based networks, Linear Discriminant Analysis (LDA), classification tree, a combination thereof, and any other suitable supervised machine learning engine. However, as can be understood, in some other embodiments, it is intended that the trained engines 140, 440 and 640 can be trained using unsupervised where only training images are provided (no desired or truth outputs are given), so as to leave the trained assessment engines 140, 440 and 640 find a structure or resemblances in the provided training images. For instance, unsupervised clustering algorithms can be used. Additionally or alternately, the trained assessment engines 140, 440 and 640 can involve reinforcement learning where the trained assessment engines 140, 440 and 640 interact with example training images and when they reach desired or truth outputs, the trained assessment engines 140, 440 and 640 are provided feedback in terms of rewards or punishments. Two exemplary methods for improving classifier performance include boosting and bagging which involve using several classifiers together to "vote" for a final decision. Combination rules can include voting, decision trees, and linear and nonlinear combinations of classifier outputs. These approaches can also provide the ability to control the trade-off between precision and accuracy through changes in phenotypes. These methods can lend themselves to extension to large numbers of localized features. In any case, some of these engines may require human interaction during training, or to initiate the engine, however human interaction may not be required while the engine is being carried out, e.g., during assessment of a Raman emission signal. See Nasrabadi, Nasser M. "Pattern recognition and machine learning." Journal of electronic imaging 16.4 (2007): 049901 for further detail concerning such trained engines.

Example 1—Feature Engineering Applied to Intraoperative Raman Spectroscopy Sheds Light on Molecular Processes in Brain Cancer: A Retrospective Study of 65 Patients Raman Spectroscopy is a promising tool for neurosurgical guidance and cancer research. Quantitative analysis of Raman signal from living tissue is, however, limited. Their molecular composition is convoluted and influenced by clinical factors, and access to data is limited. To ensure acceptance of this technology by clinicians and cancer scientists, the analytical methods needed to be adapted to more closely model the Raman-generating process. The objective is to use feature engineering to develop a new representation for spectral data specifically tailored for brain diagnosis that improves interpretability of the Raman signal while retaining enough information to accurately predict tissue content. The method consists in the band-fitting of Raman bands which consistently appear in brain Raman literature, and the generation of new features representing the pairwise interaction between bands and the interaction between bands and patient age. The technique presented in this example was applied to a dataset of 547 in situ Raman spectra from 65 patients undergoing glioma resection. It showed superior predictive capacities to a Principal Component Analysis dimensionality reduction. After analysis through a Bayesian framework, oncogenic processes most important in the differentiation between glioma and normal brain were identified: increased nucleic acid content, overexpression of type IV collagen and shift in the primary metabolic engine. The results demonstrated in the following example shows how such mathematical transformation of the Raman signal can allow a statistically robust biological analysis of in vivo Raman spectra from brain tissue.

Raman spectroscopy can recognize brain cancer cells in vivo during brain surgeries. Following recent integration in portable surgical tools, Raman spectroscopy holds significant potential to address a shortcoming in cancer research and diagnosis: the interrogation in real-time of human cancer cells in situ.

With animals and ex vivo models, we have come a long way to identify molecular processes in brain cancer. In order to survive and proliferate, cancer cells adapt their behavior and environment in a highly complex but predictive way, making it possible to track down their presence using specific metabolic biomarkers. In glioma, the most prevalent form of brain cancer worldwide, these processes include, among others, neovascularization, hypoxic energy production, enhanced cell motility and replication, and genetic mutations. All of these perturb the tissue surrounding cancer cells and make glioma detection with Raman spectroscopy possible.

Indeed, the Raman spectrum relays a signal pertaining to proteins, cell membranes, nucleic acids and lipids, which are straightforward to identify in a controlled setting where only few molecules interact, and where thousands of Raman acquisitions can be performed. In medical applications, these conditions do not hold; live tissue is chaotic, and accessibility to data is expensive. Whereas most of the research on adapting Raman spectroscopy for in vivo diagnosis has focused on technical aspects of the systems, not much has been challenged in terms of analytical methods.

A spectrum, however, is only one possible representation of the Raman signal. This "spectral" representation is convenient—but when automatizing the analysis of signals acquired in biomedical settings, its many pitfalls become evident: it can contain mostly noise, may not account for interactivity between bands, and may not integrate clinical information about the tissue nor patient being tested. These limitations hinder one's ability to quantify molecular content of a sample from its Raman signature.

The Raman signal of biological tissue is both hierarchical and interactive. Hierarchical because vibration modes belong to molecules, which are themselves part of cellular or extra-cellular structures and mechanisms, all coming together to generate the hundreds of variables that compose a Raman spectrum. Interactive because molecules do not act alone. Among them, age is the most studied: older brains accumulate protein, lipid and carbohydrates deposits and undergo progressive genomic damages. Traditional analysis of biological Raman data involves abstracting away all this complexity and relying on machine learning models to mathematically learn the spectral patterns that map one spectrum to pre-defined labels (e.g., cancer tissue vs normal tissue). These data-oriented approaches work well in settings where the number of observations greatly exceed the number of variables, which may not the case in biomedical studies. While Raman spectra can exhibit from 500 to 1,000 variables, published studies include no more than 30 patients; access to human tissue is limited and labeling of tissue by expert pathologists can be costly. Furthermore, data-driven methods are agnostic of domain-knowledge such as context, important spectral regions, and clinical information. Incorporating domain-knowledge into bio-spectroscopy analysis is poorly explored by fear of introducing subjective bias in a sterile statistical analysis. Although it is known that Raman can distinguish tissue phenotypes based on machine learning approaches, there remains room for improvement, especially in robustly deconstructing and quantifying the molecular composition of living tissues based on their Raman signal, limiting the power of Raman spectroscopy as a tool for in situ metabolic research.

In this example, a new method is suggested to transform the Raman spectral information into a format that is interpretable and amenable to robust statistical analysis. This example shows how the methods and systems described herein can allow to account for the hierarchical and interactive structure of the Raman signal and control for clinical information by dramatically reducing the size of Raman data, all while preserving predictive power when compared to previous modeling strategies. This method was applied to a dataset of 547 human brain and glioma Raman measurements acquired in situ during 65 different neurosurgical resections and use a multivariable Bayesian statistical model to shed light on the cancer-specific mechanisms amenable to Raman systems in living brain cancer.

Patients were selected by a single neurosurgeon during the years 2014 to 2018 at the neuro-oncology department of the Montreal Neurological Institute and Hospital (Quebec, Canada). In total, 135 brain cancer patients were operated while using a handheld point-probe Raman spectroscopy systems, of which 65 suffered from glioma grade II to IV. The diagnosis of excluded patients included meningioma, lymphoma and metastases.

The Raman interrogations presented herein occurred during the development of a probe designed to assist neurosurgeon in tumor resection procedures. During the 4 years of acquisitions, the acquisition systems including hardware and software evolved, acquisitions protocol slightly changed, and quality control became more rigorous. This time-dependent heterogeneity in the data is characteristic of any emerging technology and engenders considerable challenges when developing analytical solution that depend on large datasets. Some of the data had previously been published.

Data acquisition protocol and system specifications were similar in all patients and have been previously described. Briefly, the surgeon first planned the approach using pre-operative Magnetic Resonance Imaging (MRI), which he/she used to guide the surgery in combination with Neuronavigation (Stealth Station; Medtronic). Raman measurements were performed in the trajectory of the surgery (an area that would be resected but appeared free of visible cancer to the operating surgeon), inside the tumor (as per the assessment of the surgeon informed by Neuronavigation), or at the surgical margin after maximal resection. After every Raman acquisition, the interrogated area was sampled and fixed in paraffin for analysis by an expert neuropathologist. All Raman acquisitions consisted in excitation with 785 nm light source (automated power control, 30-75 mW) followed by three 50 ms Raman measurements (500 µm spot size). For all points, a 50 ms background measurement with no laser excitation was also performed.

Based on the observed degree of infiltration reported by the neuropathologist, the samples were separated under two labels. Based on neuropathologist experience, 60% cancer cell infiltration is an acceptable threshold to achieve a precise diagnosis (MCG). Thus, samples with less than 60% infiltrated cancer cells were labeled as normal brain; this represented brain samples in which some individual cancer cells were present, but no strong cancer organization had taken form. Samples with >60% infiltrated cancer cells were labeled with a cancer phenotype; these were samples where cancer was dense, organized and likely to have developed strong extracellular adaptive mechanisms such as neovascularization and intercellular pro-oncological signaling pathways. To the inventors' knowledge, this is the largest dataset of in vivo, neurosurgical human Raman spectroscopy (FIG. 9).

Figure 9:
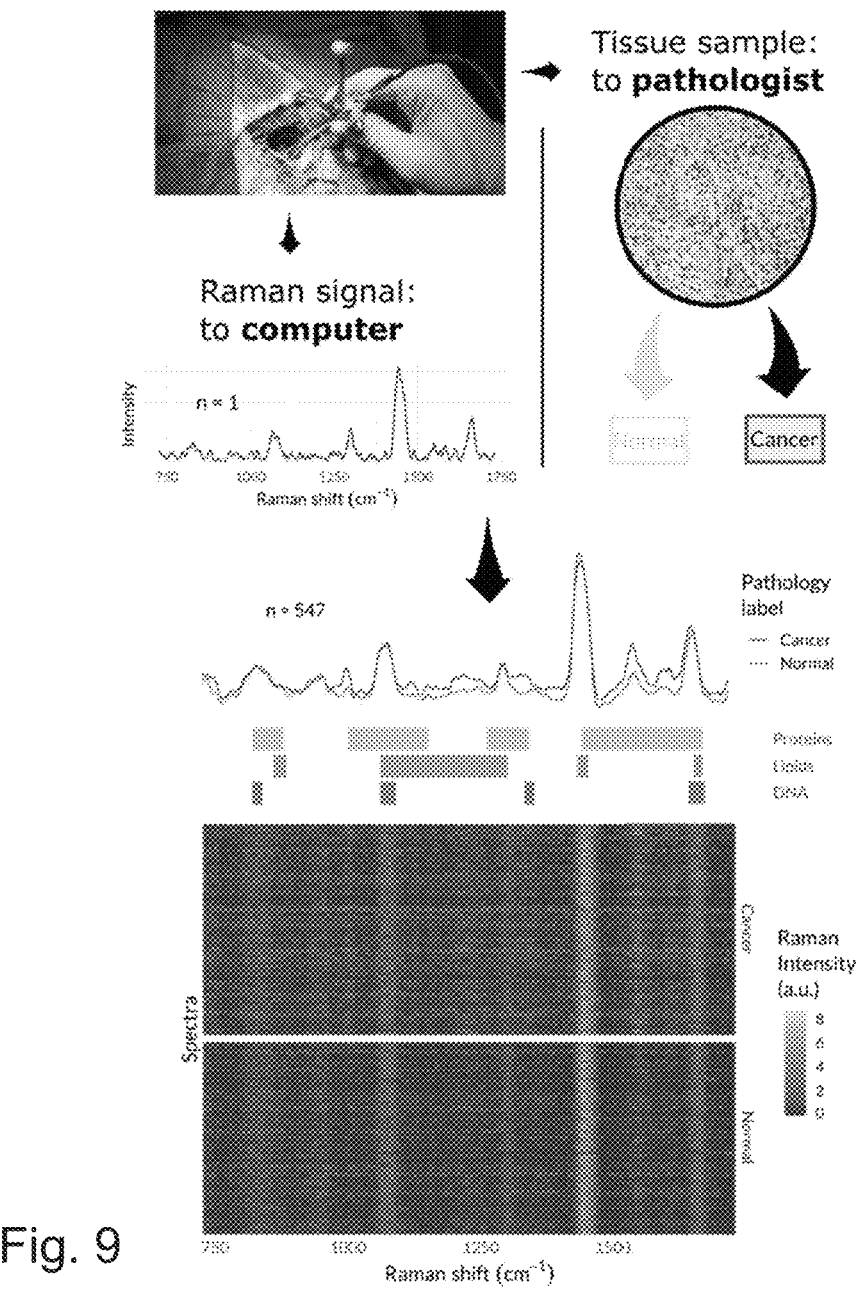
FIG. 9 shows another example of an implementation of a method of assessing a phenotype of a portion of a biological tissue using a fiber-optic Raman probe, in accordance with one or more embodiments.

FIG. 9 shows a depiction of the workflow used for the acquisition of the Raman spectroscopy data, where "a.u." denotes "arbitrary units." More specifically, the signal was acquired with a Raman handheld point-probe by a single neurosurgeon. After acquisition, the interrogated region was resected and processed for analysis by a neuropathologist. According to the percentage of infiltration in the sample, the spectrum was labeled as "Cancer" (>60% of glioma cells) or "Normal" (<60% of glioma cells).

All raw signals, as detected by the CCD camera during acquisitions, were re-processed according to a state-of-theart signal processing pipeline written in Python (version 3.6.5, 2018). First, the background signal (measurement acquired with laser turned off) was subtracted and the resulting spectrum was corrected for system response by normalizing to a measurement made on a Raman standard (SRM2241; NIST, Gaithersburg, Maryland). Afterwards, remaining low-frequency background (mainly tissue autofluorescence) was removed with the help of the Rolling Ball algorithm (ball width: 51 points). The spectrum was truncated to remove artifacts introduced by the Rolling Ball algorithm at both ends (e.g., 150 points may be removed on each side), for a final spectral range of 728 to 1730 cm$^{-1}$. A Gaussian filter was applied (p=0.5). Finally, the spectrum was normalized with standard variate normalization (SNV) to have a mean of zero and standard deviation of one, and then the minimum was subtracted in order to keep all intensity values above zero. After signal processing, the full Raman spectrum contained 560 variables.

All spectra were also evaluated on their quality by three blinded, independent reviewers (EL, FD, GS) on the LabelBox platform (San Francisco, CA). Specific criteria were used such as: gross signal-to-noise ratio, peak prominence and biological susceptibility of peak location (reference peaks were the phenylaniline peak at 1004 cm$^{-1}$, the nucleic acid peak at 1082 cm$^{-1}$, the amide III peak at 1300 cm$^{-1}$, the $CH_2/CH_3$ deformation peak at 1441 cm$^{-1}$ and the amide I peak at 1659 cm$^{-1}$). Spectra were classified on a scale of 1-3, and the sum for all reviewers was kept as the final quality assessment. A score of 5 or superior was decided as "high-quality."

Patient age was recorded for all acquisitions. Because of its bimodal distribution and to increase statistical power, the variable was dichotomized to "Young" and "Aged" at the median age of 52 years.

The feature engineering method to change the representation of the Raman signal into one that is interpretable and amenable to statistical analysis involved two steps: 1) first feature extraction and 2) mathematical interaction to generate new, second features.

First, high-yield information were extracted from the processed Raman spectra to create a compressed representation of the signal that is easier to manipulate for the second step. This is achieved through band fitting of pre-specified target bands with Gaussian distributions. To select the target bands, a systematic analysis of the Raman literature between 1999 and 2019 was performed, selecting all articles that presented original experiments on brain tissue. Articles in which the authors performed tissue or spectral manipulation that would result in significantly different spectra than the dataset were removed. The exclusion criteria included paraffinization of the samples, different spectral range (high-wavenumber only), Coherent anti-Stokes Raman Spectroscopy, Surface-Enhanced Raman Spectroscopy, and articles from the inventors' own research group. From the remaining 21 articles, every mention of Raman bands from the text or figures were compiled, and after accounting for band location variability (+/−5 cm$^{-1}$), the bands were ranked based on the frequency reporting. The 15 most frequently reported bands were selected as target peaks (as this was the median number of bands reported in the articles). For each of the 15 bands, in each spectrum, the closest peak was defined in a defined region around the band (5 wavenumbers on each side), after which the first inflection points around the peak were found. A Gaussian density function was then fitted to the spectra between those inflection points using Maximum Likelihood Estimation. Specifically, the Gaussian function takes the form $$\hat{y} = ae^{\frac{-(x-m)^2}{2S^2}},$$

where $\hat{y}$ is the estimated signal and x the x-axis values (in cm$^{-1}$), a is the maximal value or peak height, s is the standard deviation or the peak-width-at-half-maximum (hereinafter referred to as "peak width"), and m is the mean or band location (which is discarded). If the estimation failed to estimate one of the parameters, the values of all parameters were imputed: the maximum value of the spectra around the target band was used as height, and deviation of the intensities around the maximum as width. After this transformation, the data contained 30 variables: a peak height and peak width value for each of the 15 target bands.

A binomial model was used to describe the probability that the interrogated sample contains cancer:

$P$(Cancer|Raman data)~binomial(1,$p$), where p is the parameter of the binomial distribution $$\binom{n}{k} p^k (1-p)^{n-k}$$

when n=1 and k is equal to 1 when the sample contains cancer and 0 otherwise.

The value of p can be expressed as a linear combination of variables. In this case, these variables included the peaks' height and width and the patients' age. The following model could be used:

$\log \text{it}(p) = \alpha + \beta_{Peak\ height} \times \text{Peak height} + \beta_{Peak\ width} \times \text{Peak width} + \beta_{Age} \times \text{Age},$ where $\alpha$ is the intercept and the $\beta$ vectors are the coefficients of the model to be estimated (the log it link restricts the output of the regression between 0-1). This model, however, treats every one of its parameters as an independent unit, whereas they should be considered as interdependent: the size of one peak affects how the other peaks should be interpreted. It is known that brain and brain cancer composition can vary with age. In the previous formula, age is considered an independent feature which directly influences the outcome (probability that the sample contains cancer), which is wrong: the patient age have no influence on the presence of cancer cells in the sample, but it does affect how the Raman spectrum should be interpreted.

A Raman spectrum hides a hierarchy: bands cluster to form peaks, groups of peaks represent molecules and molecules interact to form structures or molecular pathways. This property of a variable to influence how another variable impacts the outcome is referred to herein as an interaction, and every Raman bands has an interacting effect on the other Raman bands. This means that the predictive effect of a Raman peak can only be considered in the context of other peaks—Raman bands are not independent. In the same way, it is hypothesized that age has an interacting effect on the Raman signal. Interaction effects can be modeled by multiplying the interacting variables together to create a new variable.

Adding interaction terms to a model improves its flexibility, but also increases exponentially the number of variables. With a limited number of observations, the interaction terms were selected to be high-yield features that are most likely to explain the behavior of the system. In this example, confidence was put on two set of interaction terms: peak-to-peak (pairwise interaction of a peak height value with all other peak height values) and peak-to-age (pairwise interaction between age and every peak height value). Peak width was left out as a potential interactor because of the low level of evidence supporting its use as a useful feature in Raman-based phenotype prediction. Therefore, the following exemplary model was defined:

log it$(p)=\alpha+\beta_{Peak\ height}\times$Peak height$+\beta_{Peak\ width}\times$Peak width $\beta_{Peak\text{-}to\text{-}peak}\times$Peak height$\times$Peak height$+\beta_{Peak\text{-}to\text{-}age}\times$Peak height$\times$Age.

The terms on the first line of the equality are the variables for the peak height and width, and their coefficient describe the effect of these variable on the tissue content. On the second and third lines are the interaction terms between every pair of bands, and between every band and the patient age. Applying this model to the data leads to an expansion of the variables set from 30 variables to 150 variables. This model constitutes a hypothetical mathematical representation of how the Raman signal explains tissue composition. After defining this formula, it was validated against actual mathematical representations, and then used to perform inference and answer more specific questions about how Raman signal is affected by tissue phenotype.

To estimate the coefficient of the aforementioned model (and as such the quantified importance of every variable as predictor for glioma), a Bayesian filter framework was used, allowing to both improve the statistical interpretation and perform a tightly regularized feature selection. Bayesian statistics rely on probability theory to estimate the likelihood of a state or event. A priori knowledge is updated by the data during the optimization process to recover the posterior probability distribution of a parameter. The a priori distribution can be used to restrict the complexity of a model, and acts as a feature selection filter. Here, it was assumed that no extracted variable has a predictive value in identifying cancer in a sample; this will result in a sparse model, where most parameters are equal to zero and thus only truly important variables impact the predictions. Hyper-lasso priors were used on the $\beta$ coefficients, as they were demonstrated superior to other regularizing priors in cases where the number of observation is low compared to the number of variables. To recover the posterior distribution of each the parameters, Markov Chain Monte Carlo (MCMC) sampling was used, more specifically a variant of the Hamiltonian Monte Carlo algorithm called "No-U-Turn-Sampling" (NUTS) as implemented in the Stan software. The code for the statistical analysis was written in R and Stan.

Validation of the feature engineering pipeline described earlier consisted in comparison of the predictive performance with a Principal Component Analysis (PCA) dimensionality reduction method. PCA projects the data into a set of linearly uncorrelated variables called Principal Components (PC). For PCA, the data were reduced to the first 50 PCs, which expressed 85% of the variance in the data. The model comparison was performed by 10-fold cross-validation, where the dataset is split 10 times into a training set $y_{train}$ and a holdout set $y_{holdout}$. Moreover, data from a single patient are kept together into either the training or holdout set to better replicate real-life predictions, where acquisitions from a patient will not be used to train the model that will perform prediction on that same patient. The parameters are estimated on the training set, yielding the "training predictions" p($\beta_{train}|y_{train}$), and "testing predictions" are performed on the holdout set, resulting in a distribution of predictions p($y_{holdout}|\beta_{train}$). Each prediction is done with a different set of coefficients $\beta_{train}^s$ for each simulation s (or MCMC iteration s). To assess the predictive performance of the model on new data, its log predictive density (lpd) was calculated using:

$$lpd_{holdout} = \sum_{k=1}^{n} \log\left(\frac{1}{S}\sum_{k=1}^{S} p(y_i | \beta_{train}^s)\right),$$

where $y_i$ is a single observation of the holdout set (of which every observation will be part of at some point during the cross-validation process) and S is the number of MCMC simulations (here: 8,000). The lpd can reflect the accuracy of the prediction, but also the confidence in this prediction: a model that emits prediction highly concentrated around a certain value will be favored against a more conservative model which prediction are more distributed on the entire prediction range. Three models were compared: 1) PCA with 50 PC followed by binomial model with normal (uninformative) priors, corresponding to a PCA-Linear Discriminant Analysis (LDA) model, 2) PCA with 50 PC followed by a binomial model with hyper-lasso priors, and 3) the feature engineered Raman signal (band fitting followed by addition of peak-to-peak and peak-to-age interactions) followed by a binomial model with hyper-lasso priors.

Both PCA and Gaussian fitting result in a compressed representation of the Raman spectra. After PCA, the original spectra can be reconstructed by multiplying the PC scoring matrix with the variable weight associated with each feature. The amount of variance expressed in the discarded PC will affect the quality of this reconstruction. In the same manner, the information from the Gaussian fitting can be used to reconstruct the original spectra. To assess the information loss encountered during both feature reduction methods, the reconstruction error between the original (full) spectra, and the spectra reconstructed was calculated from both PCA and band fitting. The normalized root-mean-squared-error (nRMSE) was used as performance metric. The nRMSE was calculated first on the full spectra and then on high-yield regions only (i.e., at the location of the target bands defined after literature review).

To uncover the relative importance of each spectral band in discriminating normal brain and glioma samples, a Bayesian logistic regression was applied with hyper-lasso priors to the entire transformed dataset. A first run was performed with 4 chains and 4,000 iterations (1,000 burned-out) to diagnose convergence problems. Then, for inference, a single chain with 10,000 iterations (2,000 burned out) was used. To filter out uninformative variables, those for which the estimated coefficient distribution was heavily centered at zero, i.e., having a large probability of being equal to zero, were selected. The threshold was set such that if zero was part of the 50% of values with highest probability, the variable was excluded from the model. In other words, only coefficients with a 75% probability mass above or below zero are considered non-zero.

Five hundred and forty-seven brain tumor samples from 65 distinct patients were interrogated by three different Raman probe systems during neurosurgical resection of glioma between 2014 and 2018. Of the 547 samples, 223 were selected as "high-quality" by the evaluators. Of these, 98 (44%) were labeled cancer (i.e., showed more than 60% cancer infiltration). The mean age of the patients from which cancer and normal samples were collected were equivalent (50 years vs 52 years).

Twenty-one articles were identified during the literature review, and all reported bands were recorded. In total, 61 bands coincided with the spectral range of the camera (median 14 bands per article, range 3-34), and they all contained a Raman peak. The 15 most frequently reported bands constituted the final set of target bands for the Raman transformation routine (see Table 1 below). The molecular assignment for each band is derived from previous Raman experiments on biological tissue, cells or solutions. Bands assigned to nucleic acid included 829, 1087, 1339 and 1659 cm$^{-1}$. Protein bands included amino acid markers such as 1004 and 1032 cm$^{-1}$ (phenylaniline), 829, 852 and 877 cm$^{-1}$ (hydroxyproline and tyrosine), and 1339 and 1553 cm$^{-1}$ (tryptophan), amide bands such as 1659 cm$^{-1}$ (amide I), 1553 cm$^{-1}$ (amide II), and 1268 and 1300 (amide III), and a carotenoid band at 1158 cm$^{-1}$. Lipid bands were 877 (choline), 1087, 1268, 1128, 1064, 1300 (cholesterol), 1441 and 1659 cm$^{-1}$.

Table 1 shows Raman bands selected as target for the band fitting procedure, with molecular assignment based on literature. The association with tissue phenotypes is based on findings form the current study.

total of 150 variables (FIG. 10B). As a comparison, the same feature generation model applied to the whole spectrum (560 variables) would result in 157,640 variables. Considering interactions among peak and with clinical variables is only possible with the highly condensed spectral representation achieved through the band fitting procedure.

More specifically, FIGS. 10A and 10B shows extraction of an interpretable representation for Raman data. FIG. 10A shows the processed spectra is subjected to a band fitting algorithm. For each target band, a Gaussian density function is fitted to the Raman spectrum, from which the height and width of the corresponding peak is estimated. FIG. 10B shows the variables of interest that constitute the new representation. From left to right: peak height as estimated by the Gaussian fitting, pairwise (Peak-to-Peak) interactions between every target bands, and interaction of age with every target bands (Peak-to-Age).

FIGS. 11A-D show a comparison of reconstruction error and predictive performances between the Raman representation resulting from band fitting and dimensionality reduc-

| Raman band (cm$^{-1}$) | Associated bond | Assigned molecule | Molecular family | Association with tissue phenotype |
|---|---|---|---|---|
| 1659 | Amide I \| vC=C | Nucleic acids \| Collagen IV \| Unsaturated fatty acids | DNA \| Proteins \| Lipids | Cancer |
| 1441 | CH2/CH3 deformation | Lipids side chains \| Amino acids \| Cholesterol \| Cholesterol ester \| Collagen | Lipids \| Proteins | None |
| 1004 | Symmetric ring breathing \| vC—C | Phenylanaline \| Collagen IV \| Heme \| Carotenoid | Proteins | Cancer |
| 1300 | CH2 twist and wag \| Amide III | Phospholipids \| Palmitic acid \| Cholesterol \| Collagen | Lipids \| Proteins | None |
| 1064 | C—O stretch \| C—O—C symmetric stretch \| C—C stretch | Proline \| Phospholipids side chains \| Cholesterol | Proteins \| Lipids | None |
| 1339 | CH2 wag \| Ring breathing mode (DNA) | Nucleic acids \| Aliphatic amino acids \| Tryptophan | DNA \| Proteins \| Glycogen | Cancer |
| 1128 | C—C stretch \| C—N stretch \| CH2 vibration | Phospholipids \| Cholesterol \| Glucose | Lipids \| Glucose | None |
| 1268 | Delta=CH \| Amide III | Unsatturated fatty acids \| Collagen | Lipids \| Proteins | None |
| 829 | O—P—O stretch \| PO2— stretch | Tyrosine \| Proline \| Nucleic acids | Proteins \| DNA | None |
| 852 | Ring breathing | Tyrosine | Proteins | Normal |
| 877 | C—C—N symmetric stretching \| C—O—C ring | Choline \| Tyrosine \| Hydroxyproline \| Sphingomyelin | Lipids \| Proteins | Normal |
| 1032 | C—H \| CH2CH3 bending | Phenylalanine \| Collagen IV | Proteins | Cancer |
| 1087 | C—C stretch \| PO2— symmetric stretch \| C=O vibration | Phospholipids \| Nucleic acids | Lipids \| DNA | None |
| 1158 | C—C \| C—N | Collagen \| Carotenoid | Proteins | None |
| 1553 | vC=C \| Amide II | Porphyrin \| Tryptophan | Proteins | Cancer |

A Raman feature engineering algorithm was applied to the data. The spectra were first band-fitted using the 15 target bands recovered through the literature review (see FIG. 10A). The Gaussian-fitting procedure was successful in 91.3% of parameters.

Figure 11A:
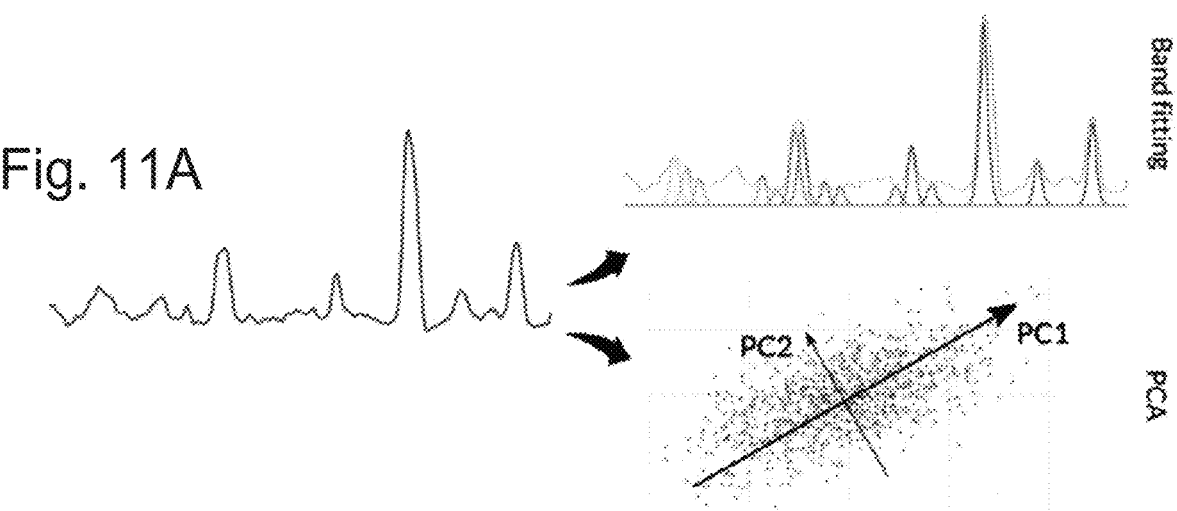
FIG. 11A shows principal component analysis (PCA) and band fitting results for an exemplary dataset of Raman spectra, in accordance with one or more embodiments.
Figure 11B:
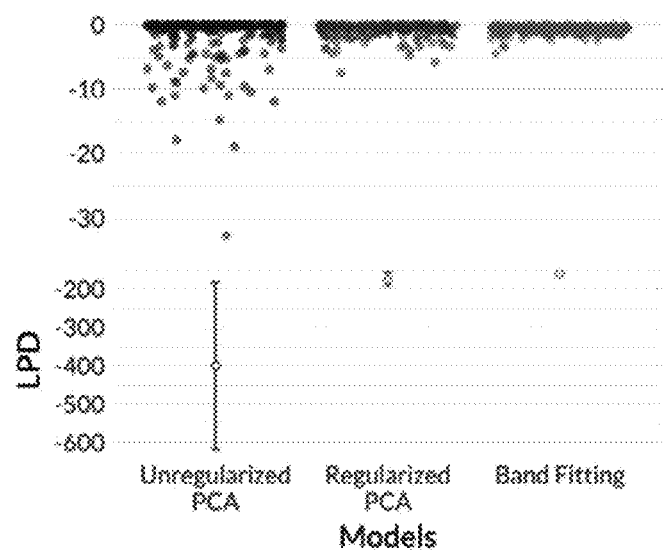
FIG. 11B is a graph showing log predictive density (LPD) for unregularized PCA, regularized PCA and band fitting results, the upper part showing LPD for every Raman spectra of the dataset and the lower part showing LPF for full dataset, in accordance with one or more embodiments.
Figure 11C:
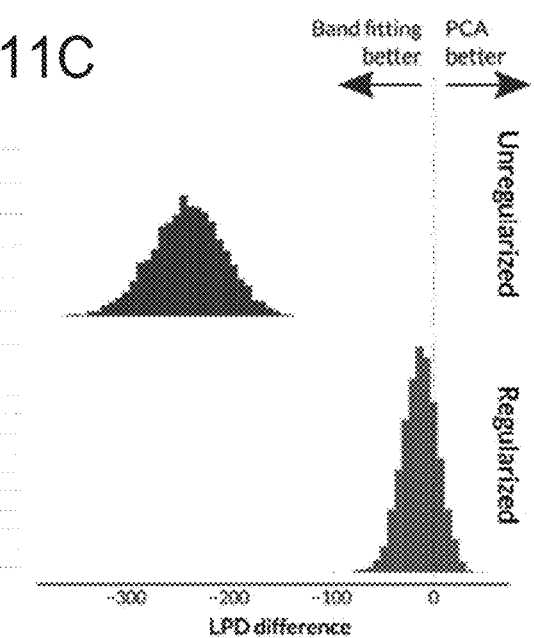
FIG. 11C is a graph showing a distribution of differences between the LPD of the band fitting and PCA representations, in accordance with one or more embodiments.
Figure 11D:
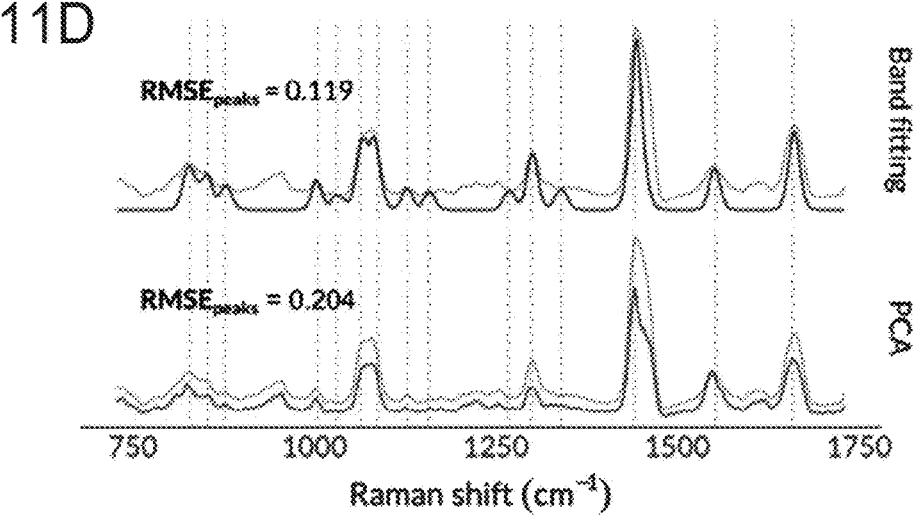
FIG. 11D is a graph showing a mean reconstructed spectra from the band fitting and PCA representations, in which values under zero represent a higher performance of the band fitting representation, in accordance with one or more embodiments.

The final feature set, including first and second features, was then generated using the model defined herein, accounting for peak-to-peak and peak-to-age interaction effects. The final feature set contained 30 variables describing the peak width and height, 105 variables for peak-to-peak interactions, and 15 variables for peak-to-age interactions, for a tion following Principal Component Analysis (PCA). More specifically, FIG. 11A shows processed Raman spectra that were subjected to both band fitting (with subsequent addition of peak-to-peak and peak-to-age interactions) and PCA with 50 principal components. FIG. 11B shows LPD for every sample (upper part of figure) and for the full dataset (lower part) during 10-fold-cross-validation. A higher total LPD signs higher predictive performances. FIG. 11C shows a distribution of differences between the LPD of the band fitting representation and PCA representation, with and without regularization. Values under 0 represent a higher performance of the band fitting representation. LPD: Log-pointwise-density. FIG. 11D shows the mean reconstructed spectra from both representations, with the reconstruction error (root-mean-squared error [RMSE]) at target bands location.

Compressing the representation of the data undoubtedly results in information loss. To evaluate the impact of this loss on potential predictive performances, the generated Raman features were compared to a Principal Component Analysis (PCA) dimensionality reduction method, the standard in Raman spectroscopy for dimensionality reduction (FIG. 11A). One objective is to demonstrate non-inferiority of the feature engineering pipeline compared to PCA for prediction on new data; as the approach to data representation optimizes biological interpretability of Raman data, equal predictive performances would still result in a superior approach over current practices.

Under a Bayesian framework, real-life training and testing of a statistical model were simulated by means of cross-validation over 8,000 MCMC simulations (see FIGS. 11C and 11D). In all of the simulations, the band fitting feature reduction method was superior to PCA with normal priors (lpd with standard error: −160.1+/−5.7 vs −400.2+/−218.3). In order to stabilize the predictive performances of the PCA method, it was applied to the same hyper-lasso priors than for the Raman transformation method. In that case, the band fitting was superior in 78.5% of the simulations (lpd with standard error: −160.1+/−5.7 vs −173.8+/−17.2). Both results demonstrate the non-inferiority of the band fitting routine against PCA, and are suggestive of even higher predictive performances.

The normalized RMSE (nRMSE) was calculated between the original data and the spectra reconstructed from both methods (PCA and gaussian-fitting)—a lowest nRMSE means a better fit. The nRMSE between the spectra reconstructed from the PCA and the original signal is 0.204, vs 0.522 for the band fitting. When considering only the target bands, the nRMSE for PCA is 0.204, while it reduces to 0.119 for the band fitting (FIG. 11B).

Figure 12:
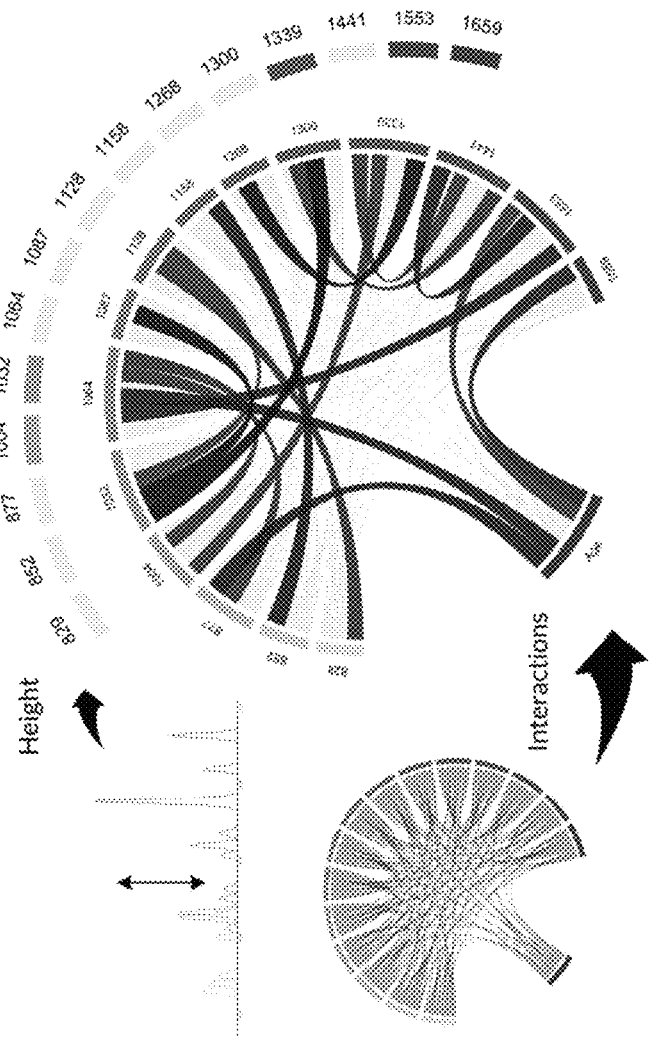
FIG. 12 shows a schematic illustration showing first and second features determined to be informative of the presence of cancer in a biological tissue, in accordance with one or more embodiments.

Next, the Bayesian logistic regression with hyper-lasso priors was applied to the entire transformed dataset. With the threshold defined in the Methods section, the model identified 30 variables as non-zero, of which 25 are depicted in FIG. 12. Important variables included peak heights, peak widths, peak-to-peak and peak-to-age interactions. To improve interpretability, variables were normalized according to their mean and standard deviation; when interpreting the coefficient of a single variable, all the other variables were assumed to be equal to zero (i.e., equal to the mean).

More specifically, FIG. 12 shows Raman spectral features from the new representation selected as probably (>75%) informative of the presence of cancer in a sample by the multivariate analysis when controlling for peak width. Outer ring: colored bars represent peaks for which the height was selected as an important variable. Inner circle: dark links represent the interaction terms (peak-to-peak and peak-to-age) that were selected by the model. The width and darkness of the link correlates with the size of the probability (darker and larger links are more probable).

For seven bands, peak height had a high probability of association with the outcome (cancer vs normal brain). Five peaks were higher in cancer (1032 $cm^{-1}$ [probability of this association: 78.4%], 1339 $cm^{-1}$ [86.0%], 1004 $cm^{-1}$ [89.0%], 1553 $cm^{-1}$ [95.6%] and 1659 $cm^{-1}$ [97.8%]), and two were higher in normal tissue (877 $cm^{-1}$ [86.5%] and 852 $cm^{-1}$ [99.1%]) (Table 1). These bands are markers of the same few oncological mechanisms: increased cellular replication, enhanced cell motility, and neovascularization.

Malignant tissue overexpresses nucleotides. In glioma, this reflects cancer cell proliferation, reactive gliosis of surrounding tissue, or even the modification in the energetic engine of the tumor. Bands at 1659 and 1339 $cm^{-1}$ are markers of nucleic acid content, and in the data, increased height was indicative of cancer. Therefore, the Raman probes successfully detected an increased proportion of nucleic acids in glioma tissue.

Raman signal of the samples was also rich in collagen-specific bands, more specifically collagen type IV, which showed higher intensity in glioma. These bands are located at 1659, 1004 and 1032 $cm^{-1}$. In the brain, collagen type IV forms the extracellular matrices and lines the extraluminal vessel wall; both of which are upregulated in cancer. Indeed, malignant cells grow in a hypoxic environment and require an increased number of blood vessels to satisfy their increased metabolic needs. But this new vasculature is poorly efficient, and cells are forced out of the tumor focus via the extracellular matrices, which offer efficient migration tracts to a less toxic environment. In addition, the peak at 1553 $cm^{-1}$ was also increased in glioma samples, and is associated with the porphyrin composing heme, further supporting the sensitivity of Raman to neovascularization.

Of the 30 variables selected by the model, 11 were peak-to-peak interactions (FIG. 12). These variables represent a synergy between two bands: either because they are expressed by the same molecule or they embody antagonistic mechanisms. Many of these bands are associated with collagen or collagen-associated amino acids (829, 852, 877, 1004, 1032, 1064, 1158, 1268, 1339 and 1553 $cm^{-1}$), supporting the importance of this substrate in live Raman acquisitions. A few pairs of peaks denote an interaction between the concentrations of lipids and proteins (1004:1064 $cm^{-1}$, 1441:1553 $cm^{-1}$, 1339:1441 $cm^{-1}$, 1032:1087 $cm^{-1}$).

Figure 13:
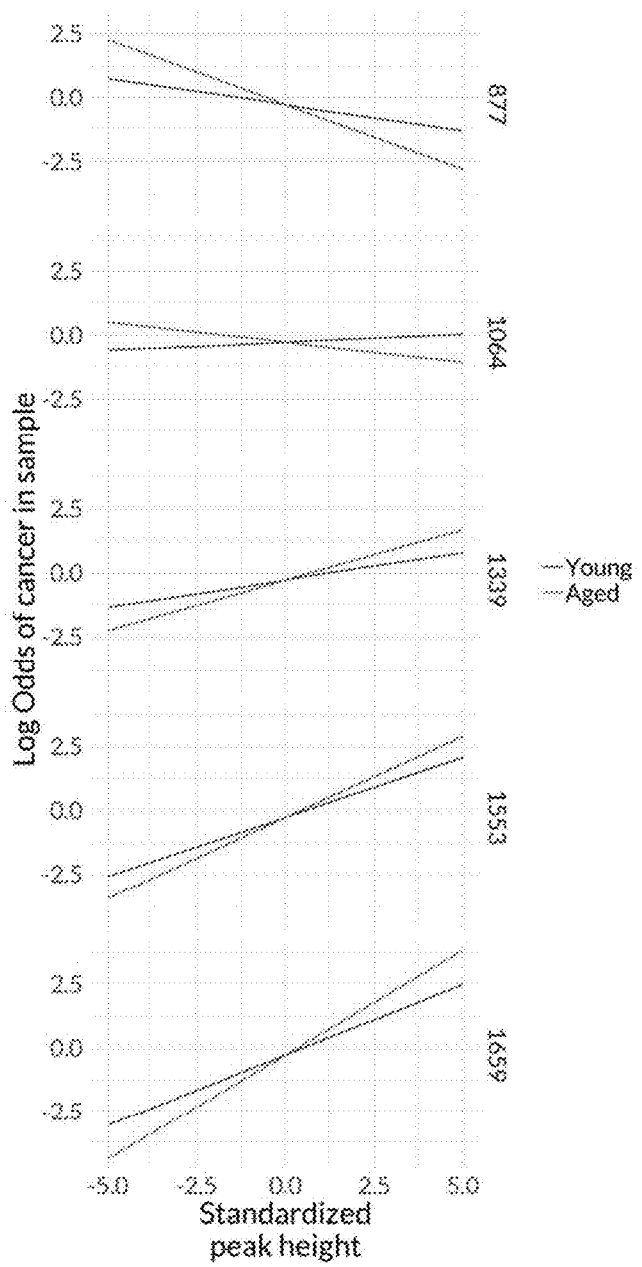
FIG. 13 is a graph showing odds of cancer in a biological sample versus standardized peak height, in accordance with one or more embodiments.

The model selected 5 age-to-peak interactions from the data (FIG. 12). These peaks relate to the presence of nucleic acids (1339 [probability of association: 74.6%] and 1659 $cm^{-1}$ [83.8%]) and proteins (877 [87.0%], 1064 [86.1%] and 1553 $cm^{-1}$ [75.3%]). FIG. 13 illustrates the effect of these interactions. The normal ageing brain accumulates protein, lipid and carbohydrates deposits, and undergo significant genomic alterations that may be amenable to Raman spectroscopy such as methylation and DNA damages. Age can also be a proxy for many conditions that affect brain constitution. IDH mutation, for example, is detectable by metabolic imaging and possibly by Raman spectroscopy, and is highly correlated with age, especially in the dataset (r=−0.72, p<0.001).

FIG. 13 shows the interactive effect of age on selected Raman bands. The slope of the association between the height of the peak and tissue type changes depending on the patient's age. If age was added as single variable, only the intercept would be affected.

A new representation is thus proposed for spectroscopy data applied to Raman spectroscopy of in situ human glioma. This representation can be specific to the Raman signal of the brain, can account for the hierarchical structure in the data and can allow the integration of clinical information such as patient age. It was demonstrated that this representation is more compact, and can minimize information loss even with modest datasets characteristic of biomedical experiments.

The predictive capacities of Raman spectroscopy in neurosurgery has already be demonstrated many times, but their mechanisms remain imprecise. The in vivo Raman literature fails to answer fundamental questions in this regard: for instance, which Raman bands are the most informative? Which Raman bands operate in unison? Does patient characteristics affect the Raman acquisitions? While this information is not necessary to predict tissue phenotypes in highly controlled environments, it can become important when 1) expecting good predictive accuracy in real surgical situations, where acquisition time is reduced, tissue uncertainty is increased, and many confounding factors (ambient light, blood, probe manipulation) lower the confidence in the Raman data, and 2) perform robust chemometric analysis of in situ human cancer based on its Raman spectrum, which requires disentangling all biologically relevant information present in the data. Attempts at band fitting and chemometric analysis of biological spectra have been avoided due to the lack of certitude in the data and a fear of overly simplifying complex and convoluted molecular processes to the point of losing most of the information behind the molecular signature. The high quality of the selected Raman spectra and the fact that important Raman bands are reproducible between study groups made the reliance on band fitting possible, lending the Raman data to be amenable to statistical analysis while preserving predictive power.

The new representation presented herein can be better than PCA to predict tissue phenotype on new, unseen patients. It can accurately retain Raman information from high-yield regions of the spectrum, regions that are consistent across research groups, experimental settings and acquisition systems. It is also able to capture interactions between variable and integrate clinical information, both which are completely obscure for PCA. Like PCA, the band fitting procedure was not biased by the data at hand—all Raman spectra were processed the same, using a priori information available before the analysis. But in the case of band fitting, this information is derived from Raman expertise in brain tissue.

Targeting specific Raman regions allowed to significantly simply the spectra, reducing the number of variables from 560 to 30. This step is mandatory to include interactions with other peaks and with age, because of the quadratic increase in the number of variables (more specifically, for n peaks, peak-to-peak interactions yields $$\frac{n(n-1)}{2}$$

variables) in the context of a few hundred observations. Having variables more numerous than observations is problematic when establishing a statistical model for the data, and is commonly referred to as the curse of dimensionality. In Raman, this high-dimensionality results in many variables being associated with the outcome only by chance. Here, regularization of the model—purposefully limiting the flexibility of the model to avoid a close fit but improve generalizability to new data—allows to counter these problems and involves two "filtering" steps: the band-fitting feature extraction and the Bayesian hyper-lasso priors.

First, only Raman regions with a high probability of being informative to the problem at hand (i.e., extracting a biomolecular fingerprint of brain and glioma tissue) are extracted from the spectra. Raman spectroscopy suffers from low signal-to-noise ratio, and unfortunately, most of the raw signal is background noise (mainly tissue autofluorescence). While signal processing algorithms allow to correct this artifact, uncertainty remains as to which part of the processed spectra constitutes true Raman signal. Allowing the definition of important Raman regions based solely on the own dataset would risk identifying as important a peak that is a consequence of hardware artefact, signal processing, acquisition conditions or probe manipulations—all which the model presented herein should ignore. Confidence can be put in features such as peaks that are reproduced by multiple independent research groups, with different systems, tissue types and acquisition parameters. By focusing on high-yield Raman bands, the feature reduction method specifically discards potentially helpful, but more probably confounding and noisy information contained in other part of the spectrum.

The second step of regularization is embedded into the statistical analysis procedure. During optimization of the Bayesian logistic regression, most of the variables will be equal to zero at any point, with only a few allowed to escape the hyper-lasso priors at the same time. This strategy is extensively used in computational statistics, and genetic studies, which suffer from the same curse of dimensionality, have used it to improve accuracy and stability of their analysis. In fact, regularization should be considered every time one cannot model the exact data-generating process.

The major drawback of the high regularization used here is the restriction in the number of variables—the higher this number, the lower the value of individual coefficients. If the uncertainty around coefficients is prominent, the number of coefficients that can escape zero is reduced, leading to equivocal results. This reason can explain why only age could be included in the analysis and no other clinical factors, why higher-order interactions were not explored and why peak width was not made an interacting variable. While the model presented in this example is plausible, its complexity is limited by the amount of data available. The results presented herein can confirm the interest of peak-to-age and peak-to-peak interactions, but more complex interaction terms will need to be investigated with larger, independent dataset to ensure the reproducibility of this model. Given more data, the proposed method can be extended to include many other potential predictors and interactors: spectral regions other than peaks (e.g., valleys, slope), higher-order interactions (e.g., three, four peaks interactions), and other clinical parameters (e.g., patient sex, comorbidities, oncological and surgical history).

The proposed model may be better than previous technique for Raman-based tissue prediction, but its true strength lies in its interpretability: the band fitting method allows to inquire the contribution of every variable to the model in a way that previous techniques cannot. Although PCA supplies the relative amount of variance expressed by each variable, its use to identify important variables has severe limitations: when doing so, it is assumed that all variables are independent, and that variance is correlated with outcome. However, most of the bands in a Raman spectrum can contain mostly noise, or are consequences of phenomena not specific to the task at hand. Also, the estimates provided by PCA are point estimates—single values, without a hint of the confidence of these estimates. On the other hand, the data representation resulting from the band fitting procedure can be amenable to robust statistical inference and offers greater interpretability than previous techniques, opening the door to chemometric analyses of biomedical Raman spectra. Not only can it unveil variable and combination of variables that are potentially more informative in the detection of glioma cells in the sample, it can also infer the side of this association (favors normal tissue vs favors cancer), all while keeping an eye on the probability that this association holds true outside the studied population.

It was opted to perform the evaluation of the model and inference over the parameters under a Bayesian framework as a filter to discriminate useful ones of the first and second features from less useful ones of the first and second features. An alternative was to use a frequentist approach: define a null-hypothesis (here, that the Raman spectra cannot predict the presence of cancer in a sample), estimate a single-value for every coefficient, and calculate its p-value—the estimate of the proportion of times a coefficient would be equal or more extreme if the experiment was repeated an infinite number of times. In contrast, Bayesian analysis recovers the entire posterior distribution for every coefficient. It can be difficult to derive meaningful biological interpretation from the recovered spectral features; a single acquisition is 500 µm in diameter, and thus integrates over a large variance in tissue content. Indeed, a sample labeled as "cancer" is highly heterogeneous, containing vascular, necrotic, mitotic or even normal regions in the same 500 µm. This uncertainty in tissue content is superimposed to that of the molecular assignment of each Raman band; the association between each band and the vibrational mode of a molecule comes from studies that have tried to isolate a molecular process of interest and analyzed the behavior of its Raman spectra. There is uncertainty when predicting the nature of a sample or estimating the effect of each variables, and modeling this uncertainty leads to a statistical inference that is more interpretable and nuanced. In the case of model comparison, not only can it identify the model with higher predictive performances, but also the likelihood of its predictions. When estimating the effect of each variable, it can be evaluated at different probability thresholds. In this analysis, all variables (equivalently, all features) were considered with a 75% probability of association with the outcome, a threshold that allowed a good balance between weeding out unhelpful variables while avoiding throwing away a critical one. If these variables were used as predictors in a machine learning task, the cost of including an unimportant variable is much lower than neglecting a crucial one. As the dataset grow bigger and our comprehension of the signification of the Raman signal of the brain improves, it will be possible to lower this threshold and be more confident in the estimation of the effect size of each variable.

DNA content, cell migration, neovascularization and adapted metabolic engine were the most prominent and probable manifestations of cancer in the Raman spectra, but other metabolic processes can also be derived from the cancer-associated bands. For example, shifts in secondary structure of proteins and in proportion of tryptophan can also have been detected with bands 1659 and 1553 $cm^{-1}$, and 1659 and 1339 $cm^{-1}$ respectively. In Raman literature, these phenomena are inconsistent. For secondary structure, some experiments demonstrate a shift from α-helix to β-sheets, while others show the opposite. In the case of tryptophan, Raman studies (including ours) indicate an increase in its relative concentration, while recent oncology research agrees that its depletion promotes immunosuppression by cancer tissue. These discrepancies might stem from the spatial resolution of Raman systems and the high heterogeneity of glioma and could be resolved by averaging over more patients and samples.

As hypothesized, features such as peak-to-peak and peak-to-age interactions contributed heavily to the model presented in this example. It is dangerous to incorporate many features into a statistical analysis and caution must be taken when interpreting the results; still, after proper regularization and despite distribution of the effect size over many parameters, some features still exhibited a high probability of being important. Analytical methods need to replicate the data-generating process as closely as our knowledge permits. The interdependencies of spectral features is inherent to the acquired measurements, and while this study shines a light on their importance, the study of peak interactions should be addressed on its own to adequately reveal higher-order interactions (e.g., clusters of more than two peaks that vary together), and move from a one-dimensional representation of a spectrum to a hierarchical representation such as the one presented here. A similar shift in paradigm was observed in image analysis, with the introduction of deep, hierarchical architectures such as convolutional neural networks. Also, the effect on Raman of age, gender and ethnicity should also be studied prospectively. Understanding the effect of these important cofounder on the Raman data (and all spectroscopy data for that matter) will be an important breakthrough for the clinical translation of predictive models into medical practice.

This example presented a technique to improve the representation of Raman spectroscopy data for the in vivo, non-destructive molecular profiling of human glioma. The proposed representation allows to better model the convoluted Raman-generating process; it focuses on high-yield regions of the spectrum, controls for the complex interactions between spectral features and allows to incorporate clinical data into the analysis. The results demonstrated how relevant these factors are to predict the presence of cancer in target tissue, and that their implication should not be overlooked in the implementation of Raman-based surgical devices. Optical technology offers a unique opportunity to interrogate diseases in their own environment—their clinical translation will require data analysis methods adapted to the complexity of the world they try to model.

As can be understood, the examples described above and illustrated are intended to be exemplary only. For instance, the tissue can be a brain tissue, a lung tissue, a prostate tissue and the like. The scope is indicated by the appended claims.

What is claimed is:

1. A method of assessing a phenotype of a biological tissue of a patient, the method comprising:
   receiving a Raman emission signal indicative of Raman emission of a portion of said biological tissue;
   using a feature generator, determining a value of a first feature based on said received Raman emission signal;
   using a computing device,
      receiving a value of a clinical parameter associated to the patient;
      generating a value of a second feature by interacting through an arithmetic operation said value of said first feature with said value of said clinical parameter;
      using a trained assessment engine, assessing the phenotype of the biological tissue based on at least said value of said second feature; and
      outputting a signal based on said assessment.

2. The method of claim 1 wherein said receiving comprises receiving values of a plurality of clinical parameters, said generating comprising generating values of a plurality of second features by interacting said value of said first feature with said values of said plurality of clinical parameters.

3. The method of claim 1 wherein said determining comprises determining values of a plurality of first features based on said received Raman emission signal, said generating comprising generating values of a plurality of second features by interacting said values of said plurality of first features with said value of said clinical parameter.

4. The method of claim 3 wherein said assessing is based on said values of said second features.

5. The method of claim 3 wherein said assessing is based on a selection of said first and second features.

6. The method of claim 3 wherein said generating said value of said second feature further comprises interacting the value of at least one of the plurality of first features with the value of a remaining one of said plurality of first features.

7. The method of claim 1 wherein said Raman emission signal has a plurality of spectrally-spaced-apart Raman emission peaks, wherein said first feature is indicative of an intensity of one of the plurality of peaks of the Raman emission signal.

8. The method of claim 1 wherein said Raman emission signal has a plurality of spectrally-spaced-apart Raman emission peaks, wherein said first feature is indicative of a spectral width at half-maximum of one of the plurality of peaks of the Raman emission signal.

9. The method of claim 1 wherein said clinical parameter is associated to an age of said patient.

10. The method of claim 1 wherein said clinical parameter is associated to a gender of said patient.

11. The method of claim 1 further comprising propagating a Raman excitation optical beam towards the portion of the biological tissue using a fiber-optic Raman probe, said receiving the Raman emission signal following said propagating.

12. The method of claim 1 further comprising, using a user interface, displaying the assessed phenotype of the biological tissue based on said signal.

13. The method of claim 1 wherein said phenotype is one of cancerous and healthy.

14. A phenotype assessment system for assessing a phenotype of a biological tissue of a patient, the phenotype assessment system comprising:
  a Raman spectroscopy system receiving a Raman emission signal indicative of Raman emission from a portion of said biological tissue;
  using a feature generator, determining a value of a first feature based on said received Raman emission signal;
  using a computing device having a processor and a memory having stored thereon instructions which when executed by the processor perform the steps of:
    receiving a value of a clinical parameter associated to the patient;
    using an interactor, generating a value of a second feature by interacting through an arithmetic operation said value of said first feature with said value of said clinical parameter;
    assessing, using a trained assessment engine, the phenotype of the biological tissue based on at least said value of said second feature; and
    outputting a signal based on said assessment.

15. The phenotype assessment system of claim 14 wherein said receiving comprises receiving values of a plurality of clinical parameters, said generating comprising generating values of a plurality of second features by interacting said value of said first feature with said values of said plurality of clinical parameters.

16. The phenotype assessment system of claim 14 wherein said determining comprises determining values of a plurality of first features based on said received Raman emission signal, said generating comprising generating values of a plurality of second features by interacting said values of said plurality of first features with said value of said clinical parameter.

17. The phenotype assessment system of claim 14 wherein said Raman emission signal has a plurality of spectrally-spaced-apart Raman emission peaks, wherein said first feature is indicative of an intensity of one of the plurality of peaks of the Raman emission signal.

18. The phenotype assessment system of claim 14 wherein said Raman emission signal has a plurality of spectrally-spaced-apart Raman emission peaks, wherein said first feature is indicative of a spectral width at half-maximum of one of the plurality of peaks of the Raman emission signal.

19. The phenotype assessment system of claim 14 further comprising a user interface displaying the assessed phenotype of the biological tissue based on said signal.

20. The phenotype assessment system of claim 14 further comprising a user interface receiving said value of said clinical parameter.

* * * * *